United States Patent
deSa et al.

(10) Patent No.: US 10,466,194 B2
(45) Date of Patent: Nov. 5, 2019

(54) PIEZOELECTRIC BIOCHIPS HAVING FLUIDIC CHANNELS

(71) Applicants: Johann deSa, Philadelphia, PA (US); Qiliang Zhang, Houston, TX (US); Ryszard Lec, Philadelphia, PA (US); Ertan Ergezen, Allston, MA (US)

(72) Inventors: Johann deSa, Philadelphia, PA (US); Qiliang Zhang, Houston, TX (US); Ryszard Lec, Philadelphia, PA (US); Ertan Ergezen, Allston, MA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 15/543,552

(22) PCT Filed: Feb. 11, 2016

(86) PCT No.: PCT/US2016/017465
§ 371 (c)(1),
(2) Date: Jul. 13, 2017

(87) PCT Pub. No.: WO2016/130753
PCT Pub. Date: Aug. 18, 2016

(65) Prior Publication Data
US 2017/0370866 A1     Dec. 28, 2017

Related U.S. Application Data
(60) Provisional application No. 62/115,662, filed on Feb. 13, 2015.

(51) Int. Cl.
*G01N 33/543*     (2006.01)
*G01N 27/12*      (2006.01)
(Continued)

(52) U.S. Cl.
CPC ...... *G01N 27/128* (2013.01); *B01L 3/502715* (2013.01); *G01N 33/5438* (2013.01);
(Continued)

(58) Field of Classification Search
CPC ............. G01N 27/128; G01N 33/5438; G01N 27/3278; B01L 3/502715; B01L 3/5027
See application file for complete search history.

(56) References Cited

U.S. PATENT DOCUMENTS

| 7,745,211 B2 | 6/2010 | Takayama et al. |
| 2003/0143722 A1* | 7/2003 | Liu ...................... B01J 19/0046 435/287.2 |

(Continued)

FOREIGN PATENT DOCUMENTS

| EP | 1788384 A1 | 5/2007 |
| WO | WO2014028167 A1 | 2/2014 |

OTHER PUBLICATIONS

International Search Report and Written Opinion; dated May 12, 2016 for PCT Application No. PCT/US2016/017465.

*Primary Examiner* — Melanie Brown
(74) *Attorney, Agent, or Firm* — Mendelsohn Dunleavy P.C.

(57) ABSTRACT

One embodiment is a biochip having an array of biosensors for quantitative determination of protein-protein and/or antibody-antigen interactions. The array comprises at least two biosensors formed on a substrate. The biosensors can be used to detect either the same or different analytes. The biosensors may be acoustical transducers operated in the thickness shear mode of vibration, wherein the density, viscosity, and elasticity at the sensor interface can be ascertained. Additionally, a series of fluidic channels are etched to the same depth as the biosensors. The fluidic channels serve to efficiently deliver the sample to the biosensors. One or more biochips can be housed within an enclosure.

17 Claims, 32 Drawing Sheets

(51) Int. Cl.
    *B01L 3/00*         (2006.01)
    *G01N 27/327*    (2006.01)

(52) U.S. Cl.
    CPC ..... *B01L 3/5027* (2013.01); *B01L 2300/0645* (2013.01); *B01L 2300/0819* (2013.01); *B01L 2300/0887* (2013.01); *G01N 27/3278* (2013.01)

(56) References Cited

U.S. PATENT DOCUMENTS

| | | | |
|---|---|---|---|
| 2006/0016699 A1* | 1/2006 | Kamahori | G01N 33/5438 205/777.5 |
| 2006/0032312 A1 | 2/2006 | Auner et al. | |
| 2007/0037225 A1* | 2/2007 | Metzger | B82Y 5/00 435/7.22 |
| 2007/0220970 A1* | 9/2007 | Gruber | G01N 29/036 73/335.04 |
| 2008/0156100 A1 | 7/2008 | Hines | |
| 2009/0133470 A1* | 5/2009 | Whalen | B01L 3/502776 73/24.06 |
| 2011/0241491 A1* | 10/2011 | Takahashi | H03H 3/04 310/344 |
| 2012/0068690 A1* | 3/2012 | Song | G01N 29/022 324/76.39 |
| 2012/0190131 A1* | 7/2012 | Novotny | G01N 29/022 436/501 |
| 2015/0377834 A1* | 12/2015 | Salvati | G01N 29/022 435/6.11 |

\* cited by examiner

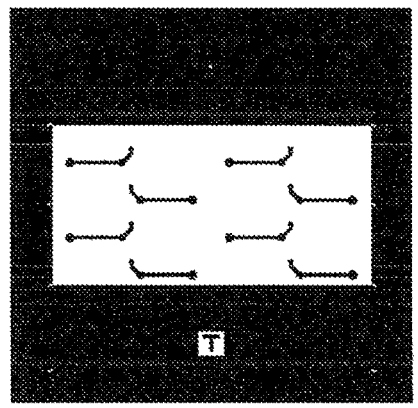 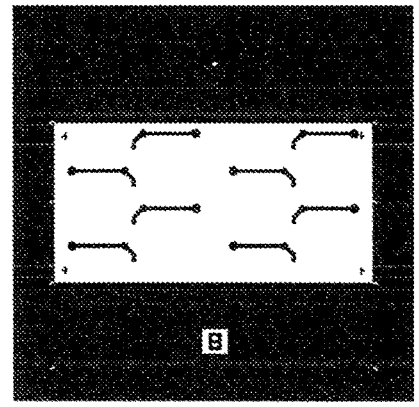
FIG. 18A  FIG. 18B
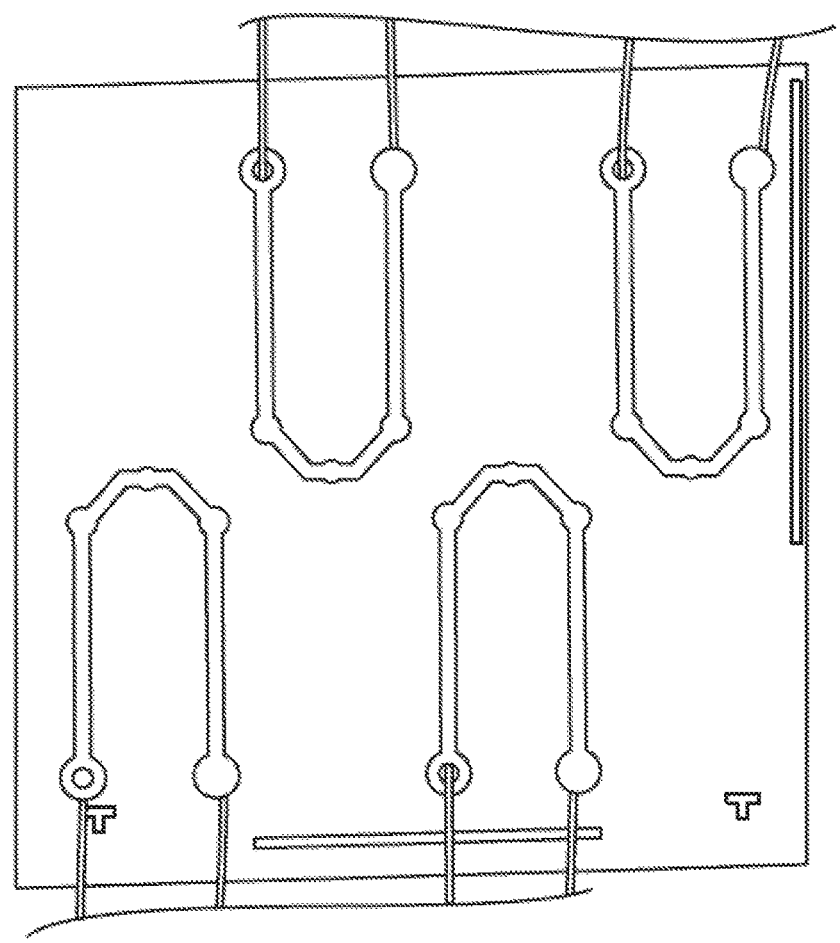
FIG. 19

Δα = change in the amplitude
Δf = change in the resonant frequency

PIEZOELECTRIC BIOCHIPS HAVING FLUIDIC CHANNELS

This application claims the benefit of the filing date of U.S. provisional application No. 62/115,662, filed on Feb. 13, 2015, the teachings of which are incorporated herein by reference in their entirety.

BACKGROUND OF THE INVENTION

1. Field of the Invention

The present invention is related to the field of sensors. In particular, but not exclusively, the present invention is related to very high frequency biosensor-based biochip systems.

2. Description of the Related Technology

Measurement reactions using a sophisticated biomolecule identification function such as an antigen-antibody, protein-protein, and protein-DNA, etc., are becoming important techniques in clinical testing, measurements in the field of biochemistry, and measurements for environmental pollutants. Some examples of this type of measurement system are micro-TAS (Total Analysis Systems), i-STAT, Q-Sense, micro combinatorial chemistry systems, chemical IC systems, chemical sensor systems, biosensor systems, microanalysis systems, electrochemical analysis systems, surface plasmon resonance (SPR) measurement systems, and attenuated total reflectance (ATR) measurement systems.

When using biochemical samples especially in, but not limited to, point-of-care rapid testing, the size of the sample to be analyzed may be small, and the concentration of the analyte may be low. It is important to be able to use a sensing system that is very sensitive and capable of working with small sample volumes.

SUMMARY OF THE INVENTION

Here, a very high frequency biochip system having and extremely high sensitivity adapted to analyze small samples is described.

In one embodiment, the present invention is an article of manufacture comprising a biochip having one or more biosensors. The biochip comprises a piezoelectric substrate having a substrate top surface and a substrate bottom surface and comprising, for at least a first biosensor, (i) a top fluidic channel formed in the substrate top surface and traversing from a top fluidic inlet to a top fluidic outlet and (ii) a bottom well formed in the substrate bottom surface and located below the top fluidic channel between the top fluidic inlet and the top fluidic outlet. The biochip also comprises a top electrode formed within the top fluidic channel on the substrate top surface and located above the bottom well; a top electrical trace formed on the substrate top surface and traversing from a top-electrode tap to the top electrode; a bottom electrode formed within the bottom well on the substrate bottom surface and located below the top electrode; and a bottom electrical trace formed on the substrate bottom surface and traversing from a bottom-electrode tap to the bottom electrode, wherein the top and bottom electrodes and the intervening piezoelectric substrate form the first biosensor.

In another embodiment, the present invention is a method for characterizing presence of a first analyte in a liquid using the biochip of the previous paragraph. The method comprises (a) applying the liquid to the top fluidic inlet of the top fluidic channel of the first biosensor such that the liquid flows along the top fluidic channel to the top electrode of the first biosensor; (b) applying an alternating electrical signal across the top-electrode and bottom-electrode taps associated with the first biosensor; (c) characterizing a vibration frequency of the first biosensor resulting from applying the alternating electrical signal; and (d) characterizing the presence of the first analyte in the liquid based on the vibration frequency of the first biosensor.

BRIEF DESCRIPTION OF THE DRAWINGS

FIG. 18A shows a top plating mask for the VHF biochip.

FIG. 18B shows a bottom plating mask for the VHF biochip.

FIG. 19 is an image of the fabricated 4-sensor VHF biochip as per designs in FIG. 15.

DETAILED DESCRIPTION OF THE PREFERRED EMBODIMENT(S)

For illustrative purposes, the principles of the present disclosure are described by referencing various exemplary embodiments. Although certain embodiments are specifically described herein, one of ordinary skill in the art will readily recognize that the same principles are equally applicable to, and can be employed in other systems and methods.

Before explaining the disclosed embodiments of the present disclosure in detail, it is to be understood that the disclosure is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel method is therefore not limited to the particular arrangement of steps disclosed herein.

It must be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

In biosensor technology developed for medical, biological, industrial, chemical and environmental applications, a biochip is the component that enables the transduction of biological and/or chemical reactions, such as antibody-antigen binding, into measurable electrical signals. The sensitivity, size, fluidics, and number/orientation, of sensors on the biochip determines the performance of a this diagnostic system, such as the system's detection limit, dynamic range, linearity, reproducibility, etc., as well as its applicability.

Each biochip may have a different numbers of biosensors. The arrangement of the biosensors on the biochip may also be changed depending on specific applications. An aspect of the present invention is a biochip having essentially the greatest or the greatest sensitivity for its intended application.

Figure 1:
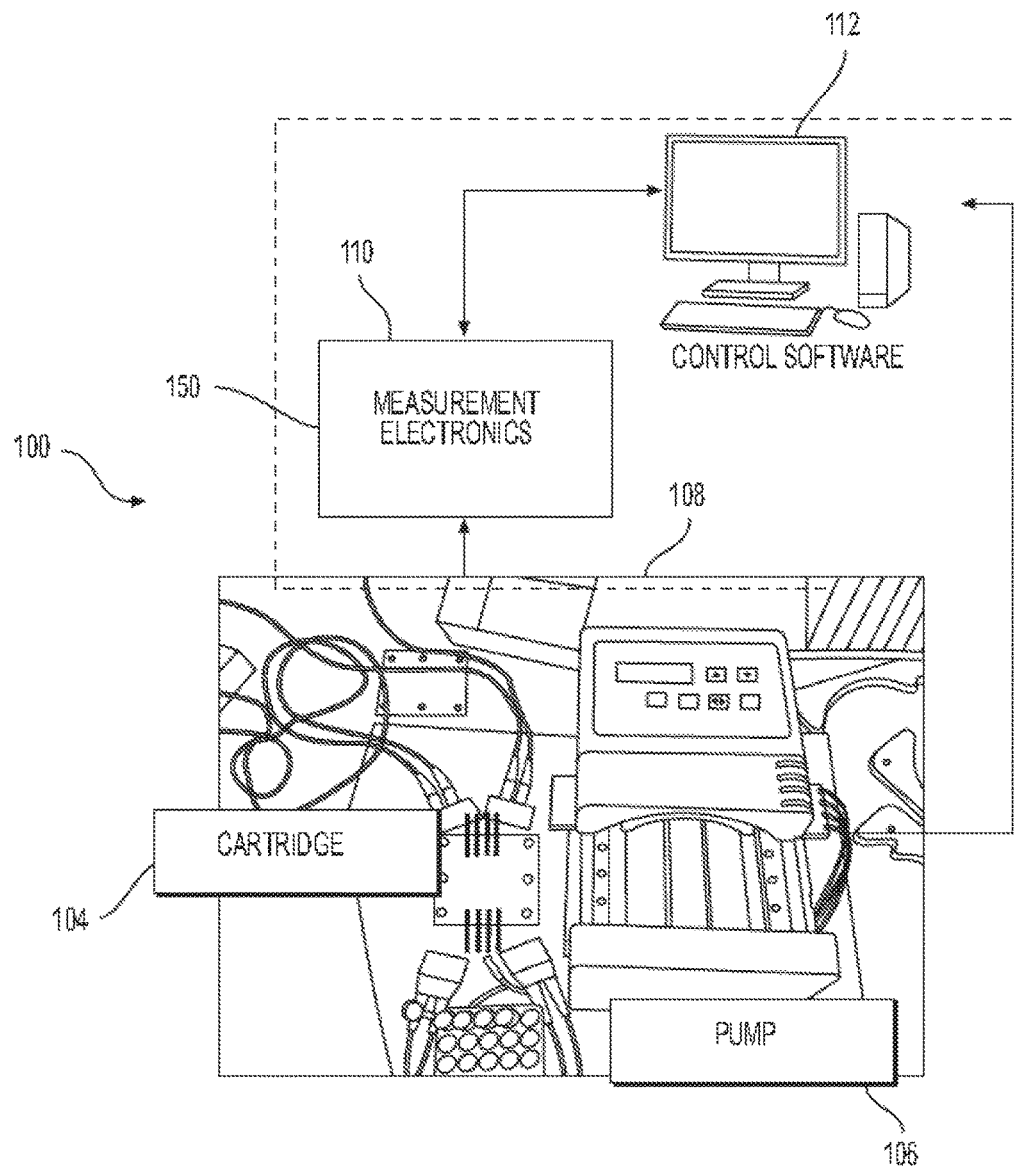
FIG. 1 shows a measurement system including a very high frequency (VHF) biochip encased in a polydimethylsiloxane (PDMS) enclosure.

An embodiment of a VHF biochip system 100 having a biochip 102 is shown in FIG. 1. In the overall system 100, biochip 102 can be a 100 MHz 4 VHF sensor chip. However it is contemplated that biochips 102 employed in the system may operate at frequencies of 50 MHz-1000 MHz. Furthermore, biochip 102 may have any number of biosensors 114 shown in FIGS. 8A-8B. For example, there may be anywhere between 1-100 biosensors 114 on a single substrate. The number of biosensors 114 depends on substrate size and frequency. For a 20 mm×20 mm 100 MHz chip, there can be 1-100 sensors.

Biochip system 100 may also comprise an enclosure 104, which, in some embodiments, can be an encapsulating enclosure; a peristaltic pump 106, which may be a 4-, 12-, or more-channel peristaltic pump; an RF switch 108, which may be a four-channel RF switch; a network analyzer 110, which may be an Agilent 4395A with an 87512A transmission reflection test set; and a computer 112. The computer 112 can be used for controlling the RF switch 108, controlling the network analyzer 110, and processing/saving data using a program such as a LabView or Matlab.

The biochip system 100 enables biological testing using biochip 102 and employs biochip testing protocols and biomarker detection protocols. The system 100 uses an array of VHF acoustic biosensors 114 for quantitative determination of protein adsorption and structural changes, cell adhesion, antibody-antigen interactions, enzyme-protein interactions, molecular interactions (DNA/RNA), lipid bilayer formation, multilayer analyte properties, biofilm formation (environmental), toxicology, drug discovery, polymer layer properties (swelling), and nanoparticle interactions. Biochip 102 may include at least 2 biosensors 114 etched into a substrate 118 that can be a blank quartz wafer, each of which biosensors 114 can be utilized to detect either the same or a different analyte. Biosensors 114 can be acoustical transducers operated in the thickness shear mode of vibration, wherein the density, viscosity and elasticity at the sensor's interface can be ascertained. Additionally, a series of fluidic channels 117 are etched to the same depth as the biosensors 114. By being etched to the same depth, fluidic channels 117 are in the same plane as biosensors 114. Fluidic channels 117 serve to efficiently deliver the sample to biosensors 114, while reducing the required sample volume and allowing for a simple protective fluidic enclosure 104.

Biochip 102 is an integration of a group of biosensors 114 that are fabricated on a substrate 118 that can be a piezoelectric substrate. The design of biochips 102 is based on considerations of many factors, such as sensor material, sensor structure, physical dimensions, and the arrangement of sensors on a chip. The resultant biochip 102 is a miniature wafer-like element capable of processing biological samples, thus integrating several components into a single component. In the present embodiment, biochip 102 comprises an array of biosensors 114 fabricated on a single quartz wafer with integrated fluidic channels 117 for sample handling.

Biochips 102 may be fabricated on AT-cut quartz ($SiO_2$) crystal substrate/discs. Among various types of piezoelectric materials, quartz crystal is chosen because of its stability, sensitivity, low cost and the availability of mature fabrication techniques for mass production. Other materials that can be used are lithium niobate, lithium tantalate, potassium dihydrogen phosphate, ammonium dihydrogen phosphate (ADP), barium titanate, zinc oxide, polyvinylidene fluoride, polycrystalline ceramic, lead zirconate titanate, lead lanthanum, and lead lanthananum zirconate titanate.

Figure 2:
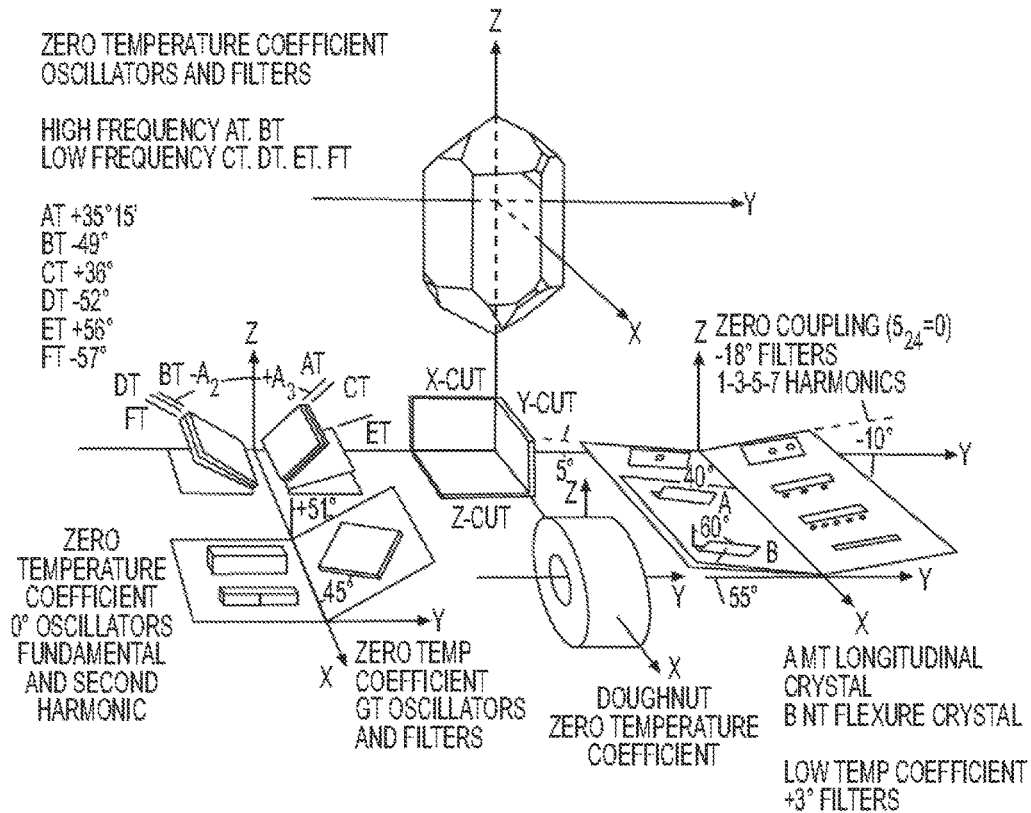
FIG. 2 is a schematic diagram illustrating different quartz cut angles.

As shown in FIG. 2, there are many ways to cut a crystal of quartz to obtain a thin slice or disc. Each cut angle is associated with different properties of the wafer. For biochips 102, an AT-cut (typically 35° 15' from the Z axis) quartz crystal is selected because it has a very low temperature coefficient, approaching to zero at 25° C. This is important for biomedical applications, which typically depend on biosensors operating in an environment at ambient temperatures of 20-25° C. This eliminates the need for temperature control modules required for other types of biosensors with higher temperature coefficients such as surface acoustic wave devices, other cuts of quartz, lithium niobate, and lithium tantalate.

Figure 3:
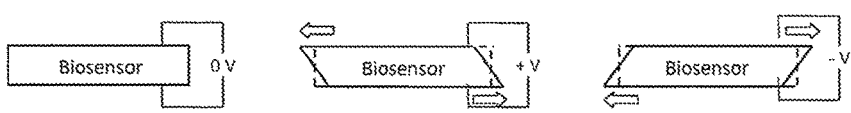
FIG. 3 is a diagram illustrating shear motions of a biosensor.

Biosensors 114 are designed to operate in thickness shear mode (TSM). As shown in FIG. 3, wherein an alternating electrical signal is applied to the top and bottom electrodes of a biosensor 114. When this occurs, the biosensor 114 exhibits shear displacements in opposite directions.

The frequency of a biochip 102 refers to the fundamental resonant frequency of biosensors 114 on biochip 102. Resonant frequency is an important parameter for biochips 102 because the mass sensitivity of a biosensor 114 strongly depends on its resonant frequency. For a biosensor 114 loaded with a thin rigid mass layer, its mass sensitivity, $\Delta f/\Delta m$, is proportional to the square of its resonant frequency, as given in Eq. (1) (Sauerbrey's equation) as follows:

$$\frac{\Delta f}{\Delta m_s} = \frac{-2f_r^2}{\sqrt{\rho_q \cdot \mu_q}} \tag{1}$$

where, $\Delta f$ is the shift in the resonant frequency; $\Delta m_s$ is the accumulated surface mass density on the sensor; $f_r$ is the fundamental resonant frequency of the sensor; and $\rho_q$ and $\mu_q$ are the density and shear modulus of AT-cut quartz crystal, respectively. Based on Eq. (1), increasing the resonant frequency of biosensors 114 can improve the mass sensitivity. However, biochips 102 with higher resonant frequencies are traditionally more costly, difficult to fabricate and handle, and exhibit higher noise in sensors and measurement electronics. These drawbacks have been overcome by the present invention. The current approach for fabricating higher frequency biochips 102 leads to significantly higher sensitivities requires extremely low sample volumes and does not significantly increase the cost of fabrication. The developed fab approach allows for an increase in the array size and the frequency from 5 MHz to 50 MHz, 100 MHz, 200 MHz, as well as up to 1000 MHz. Current VHF biochip designs consist of 2-10 50-200 MHz biosensors 114 on a single wafer 118, though it is possible to locate 100 or more 50-1000 MHz biosensors 114 on the same substrate 118. In the current design, the resonant frequency of biochips 102 is chosen to be about 100 or 200 MHz. However, it should be understood that the resonant frequency can be anywhere in the range of 50 MHz-1000 MHz.

The fundamental resonant frequency of a biosensor 114 is determined by its thickness, as given in Eq (2) as follows:

$$f_r = \frac{v_q}{2 \cdot t_q} \quad (2)$$

where $v_q$ is the acoustic velocity in the AT-cut quartz crystal and $t_q$ is the thickness of the quartz membrane.

Figure 4:
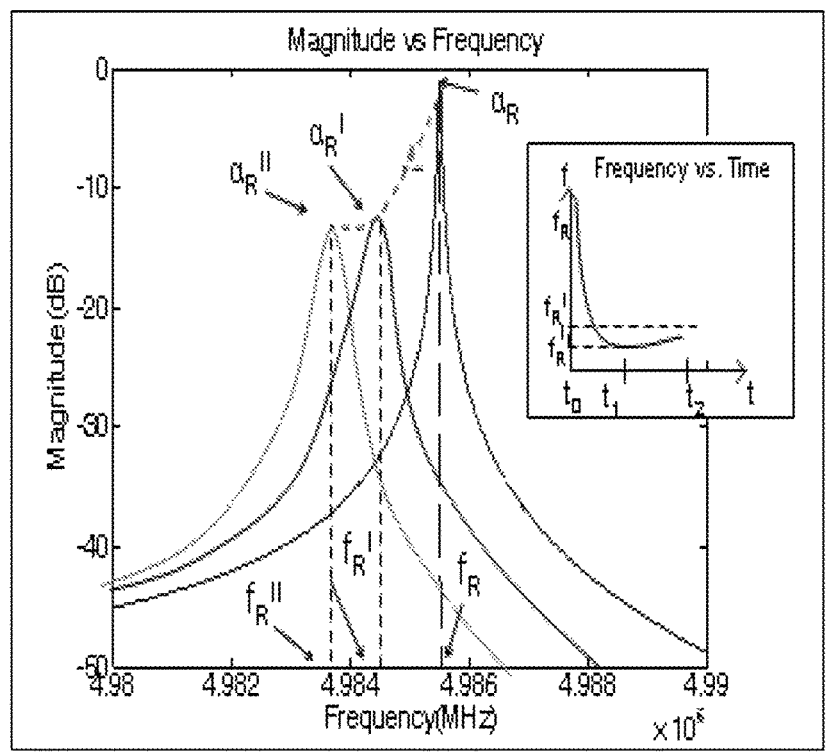
FIG. 4 is a diagram illustrating the frequency-dependent response of a VHF sensor in the vicinity of its resonant frequency.

When biosensors 114 are excited around their resonant frequency a plot similar to that shown in FIG. 4 is obtained. Upon loading with mass or liquid there is a decrease in the frequency and amplitude of resonance as seen in FIG. 4. By tracking this change, the mass loading and/or fluid mechanical properties can be determined using Eq. 1 (Sauerbrey) and Eqs. (3) and (4) (Kanazawa) as follows:

$$\Delta f_l = -\sqrt{f_0^3 \frac{\rho_l \eta_l}{\pi \mu_q \rho_q}} \quad (3)$$

where $\mu q$ is the shear modulus in the x-direction, $\rho q$ is the density of the crystal, and $\mu l$ and $\rho l$ are the modulus and density of the liquid. As used herein, the terms "liquid" and "fluid" are synonymous. In addition to the frequency shift, there also exists a damping of the resonator caused by the viscous liquid layer. Dampening due to liquid can be also be quantified in the measured series resistance in the equivalent electrical circuit given by Eq. (4) as follows.

$$\Delta R_l = 4L_q \sqrt{f_0^3 \frac{\pi \rho_l \eta_l}{\mu_q \rho_q}} \quad (4)$$

This damping factor allows the possibility to detect not only mass changes but also viscoelastic and conformational changes of interactions. This last equation contains the term Lq which describes the inductance due to the quartz (a constant).

Figure 5:
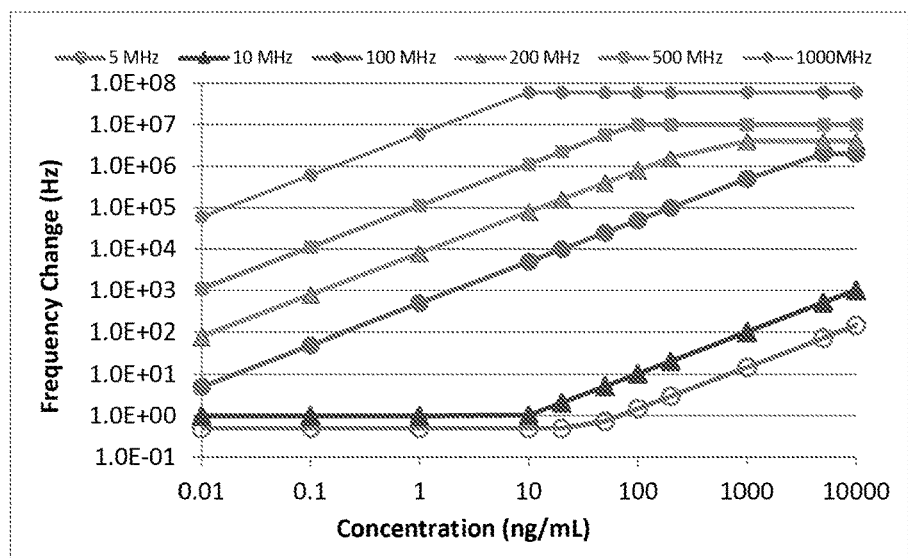
FIG. 5 is a theoretical plot demonstrating that the mass sensitivity increases with the resonant frequency.
Figure 6A:
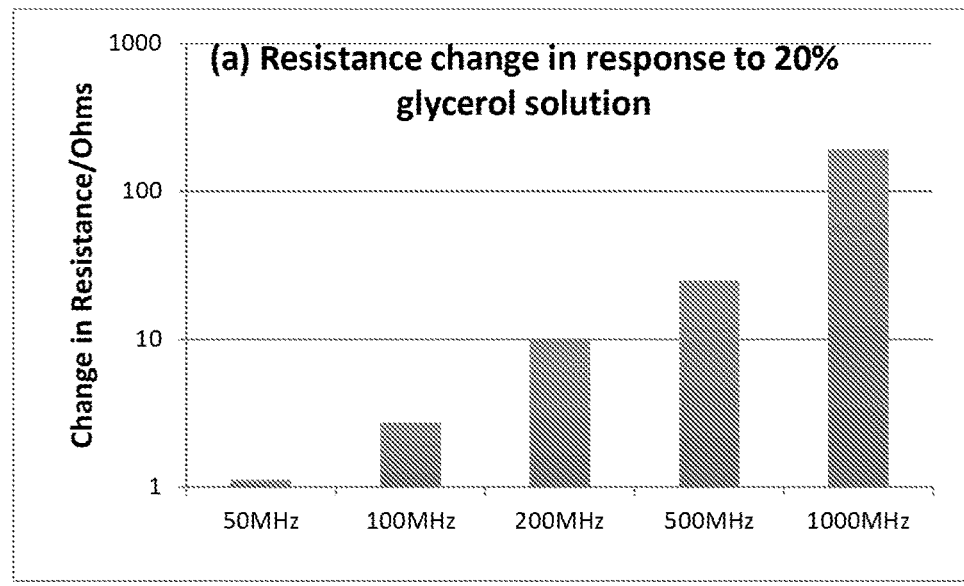
FIG. 6A is a theoretical plot demonstrating that the amplitude (resistance) sensitivity to loading with 20% glycerol increases with increasing resonance frequency.
Figure 6B:
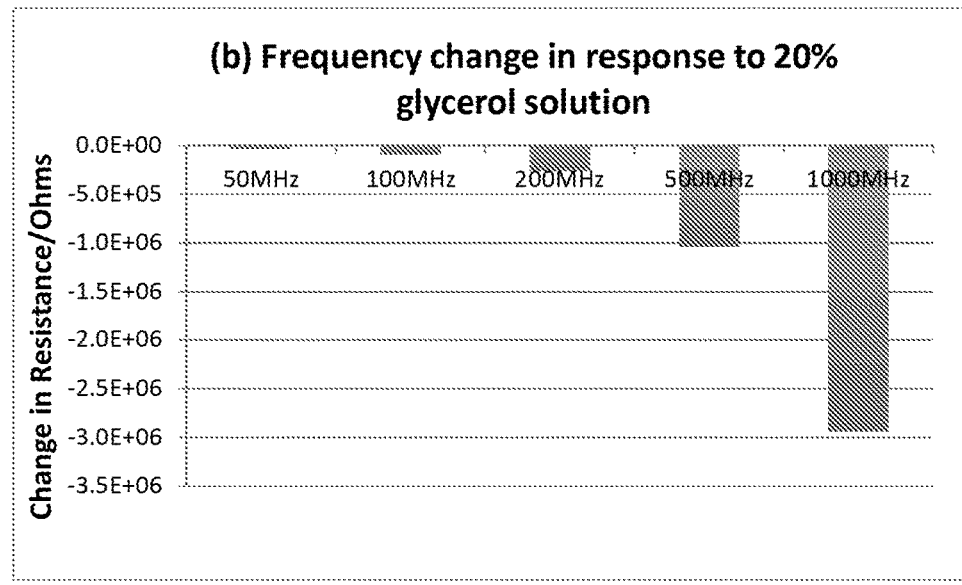
FIG. 6B is a theoretical plot demonstrating that the frequency sensitivity to loading with 20% glycerol increases with increasing resonance frequency.

Using the above equations, FIGS. 5, 6A, and 6B are plotted to demonstrate an increase in sensitivity to mass and viscoelastic loading of biochip 102 as the resonance frequency is increased from 5 to 1000 MHz.

Figure 7A:
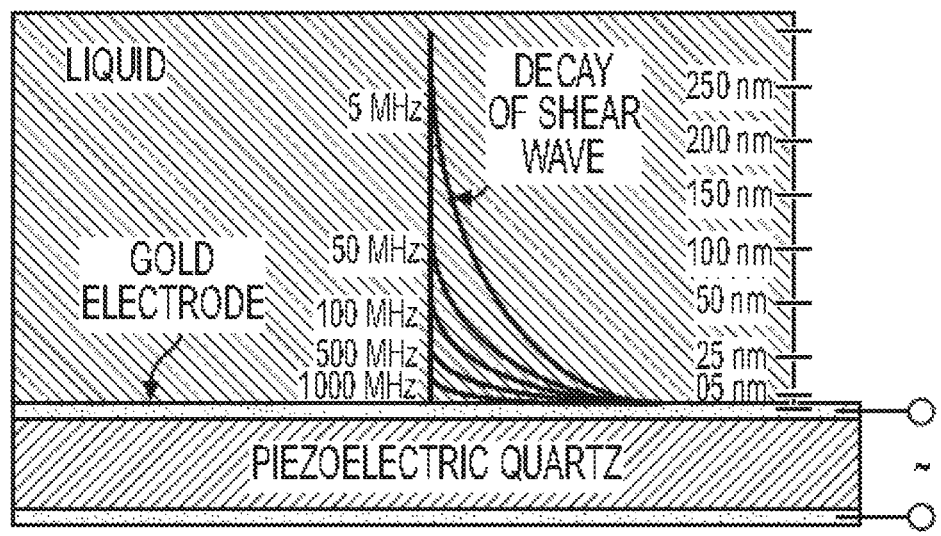
FIG. 7A is a schematic of the penetration/interrogation depth of the VHF biochip as a function of resonance frequency.
Figure 7B:
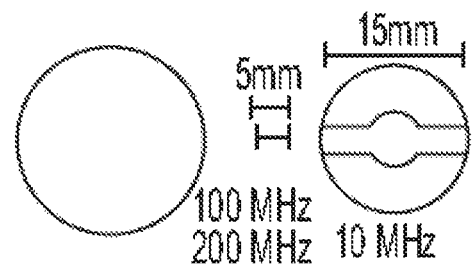
FIG. 7B is an image of the sizes of 10 MHz, 100 MHz, and 200 MHz sensors.
Figure 8A:
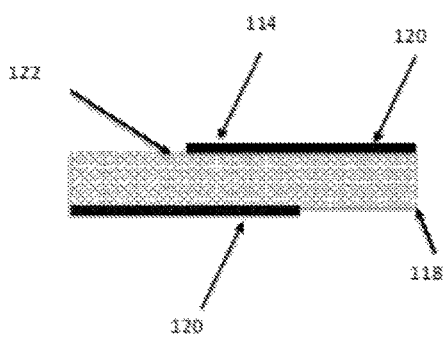
FIG. 8A is a schematic diagram showing a planar geometry of a biosensor.

Using the selected resonant frequency for biochip 102, the required thickness of the membrane 122 of the quartz can be calculated. With the acoustic velocity in AT-cut quartz crystal, $v_q$, valued at $3.336 \times 10^3$ m/s, the respective thicknesses of the membrane 122 for biosensors 114 that have resonant frequencies of 10 MHz, 100 MHz, and 1000 MHz (thickness shear mode) are 166.8 µm, 16.68 µm, and 1.668 µm respectively. Increasing the resonant frequency from 5-1000 MHz leads to a decrease in interrogation depth from 250 nm to 6 nm making biosensor 114 more and more sensitive to smaller molecules as the resonant frequency is increased. This is shown in FIGS. 7A and 7B. Increased resonant frequency comes with a thinner quartz disc, which is more fragile and harder to handle and package. In most applications utilizing biosensors 114 that are AT-cut quartz crystal TSM sensors, 5-30 MHz sensors having thicknesses from 333.6 µm to 55.6 µm are used. A typical planar structure of these low resonant frequency TSM biosensors 114 is shown in FIG. 8A. The thickness of the membrane 122 of quartz is determined by Equation 2 for a preselected sensor frequency. One electrode each is deposited on opposite surfaces of biosensor 114. For low resonant frequency (below 30 MHz) TSM biosensors 114, this planar configuration is mechanically strong enough for most applications.

Figure 8B:
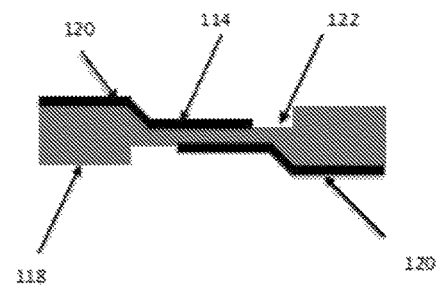
FIG. 8B is a schematic diagram showing an inverted mesa geometry of a biosensor.

However, for higher resonant frequency biosensors 114, an inverted mesa structure is often used, as shown in FIG. 8B.

In order to fabricate an inverted mesa TSM biosensor 114, such as shown in FIG. 8B, a substrate 118 of quartz crystal that is much thicker than the required membrane thickness (usually 5-100 times thicker for a 50-1000 MHz resonant frequency) is used to provide sufficient mechanical strength. Substrate 118 may be a quartz plate, or any other simple shape, that is then etched to obtain membranes with the required thickness at designated areas using etching masks.

For a biochip 102 with a 100 MHz resonant frequency, a substrate 118 of an AT-cut quartz crystal disc with a thickness of 100-150 µm was used. The quartz plate was double-side etched down to 16.68 µm at the sensor well areas.

The thickness of membrane 122 can be precisely controlled by selecting a proper combination of etching time and quartz etching rate, depending on the etching technique and/or etching solution used. Since the resonant frequency of a TSM biosensor 114 can be determined by the thickness of the membrane 122, multiple biosensors 114 fabricated on the same quartz crystal substrate 118 should have almost the same resonant frequency. Small variances in the resonant frequencies, normally smaller than 0.1%, may be observed for biosensors 114 on the same biochip 102. This variance is mainly caused by anisotropy in the quartz crystal and non-uniform etching.

VHF biochip 102 may utilize an inverted mesa structure, as shown in FIG. 8B, to ensure having a membrane 122 of thin quartz, for a high resonant frequency and mass sensitivity and enhanced mechanical strength. Besides the thickness of the membrane 122 and substrate 118 of quartz, there are two additional parameters to be considered in the design of biochip 102: the diameter of electrodes 120 and the diameter of quartz membrane 122.

Figure 9A:
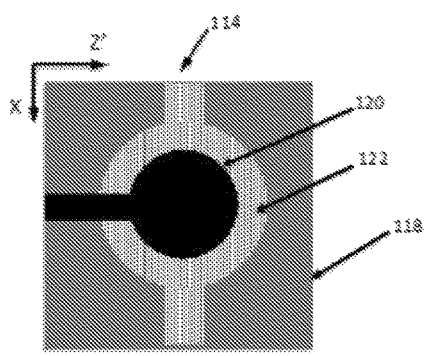
FIG. 9A is a schematic diagram showing a top view of a biosensor.
Figure 9B:
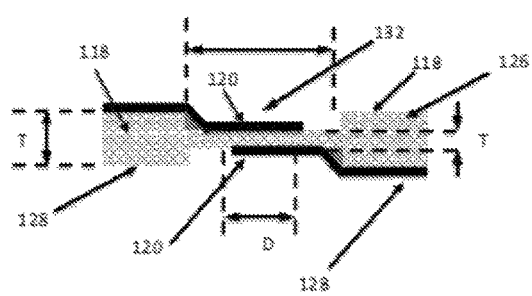
FIG. 9B is a cross-sectional schematic diagram showing an inverted mesa geometry of a biosensor.

Biosensor 114 may be a membrane 122 that is a quartz plate with two electrodes 120 that are circular chrome-gold deposited on opposite surfaces of membrane 122, as shown in FIGS. 9A and 9B. To ensure the proper generation of a thickness shear wave inside biosensor 114, there is a preferred range of the ratio of the thickness of membrane 122 to the diameter of electrode 120. If the ratio is too small (below 15), then energy trapping within biosensor 114 becomes less efficient and performance deteriorates. If the ratio is above 60, then the electrodes 120 of biosensor 114 behave more like a capacitor, and biosensor 114 is electrically shorted out and loses its capability to be a biosensor. Preferably, this ratio is about 20 for TSM biosensors 114 operating at the lower end of the frequency range. For higher frequency biosensors 114, this ratio is preferably in the range of 30-50. In the 100 MHz VHF biochip 102, the diameter of electrode 120 is selected as 762 µm or 0.030 inch, and the membrane thickness is 16.68 µm. Thus, the ratio of the diameter of electrode 120 to the thickness of membrane 122 is about 45.

The diameter of the quartz membrane 122 is also important. If the membrane diameter is very close to the electrode diameter, the boundary conditions for biosensor 114 may be changed and undesirable spurious modes may be generated inside biosensor 114. This can result in lower energy coupling and a reduced quality factor for the fundamental resonant mode, which leads to a lower sensitivity. If the diameter of membrane 122 is too large compared with the diameter of electrode 120, this can significantly reduce the mechanical strength of biosensor 114 an unacceptably increase the size of biosensor 114 and therefore reduce the number of biosensors 114 that fit on a biochip 102, which results in higher costs associated with biochip 102. The diameter of the quartz membrane 122 is preferably selected to be between 1.5-5 times the diameter of the electrode. The ratio of the diameter of the membrane 122 to the diameter of the electrode 120 is 1.4. In some embodiments, this ratio may be between 0.5 to 2, and in a preferred embodiment the ratio may be between 1.0 and 1.7, and in a most preferred embodiment the ratio may be between 1.3-1.7.

In the inverted mesa structure shown in FIG. 9B, membrane 122 is a thin quartz crystal that is coated with two electrodes 120, preferably made of gold with an adhesive layer, preferably chrome, on its top surface 126 and bottom surface 128. In order to monitor the performance of biosensor 114, electrical connections need to be made between the two electrodes 120 and an external electronic measurement system. In FIG. 9B, it can be seen that gold electrodes 120 may be placed on the top surface 126 and bottom surface 128 of the quartz membrane 122.

In order to deposit high-quality electrodes 120 on the sidewalls, electrode 120 located on top surface 126 is brought out of well 132 along the Z' direction, while electrode 120 on bottom surface 128 is brought out of well 132 along the Z minor direction in the view shown in FIG. 9A. The opposite directions, Z prime for electrode 120 on top surface 126 and Z minor for the electrode 120 on the bottom surface 128, are attributed to the mirror effect of the opposite surfaces of quartz substrate 118.

Figure 10:
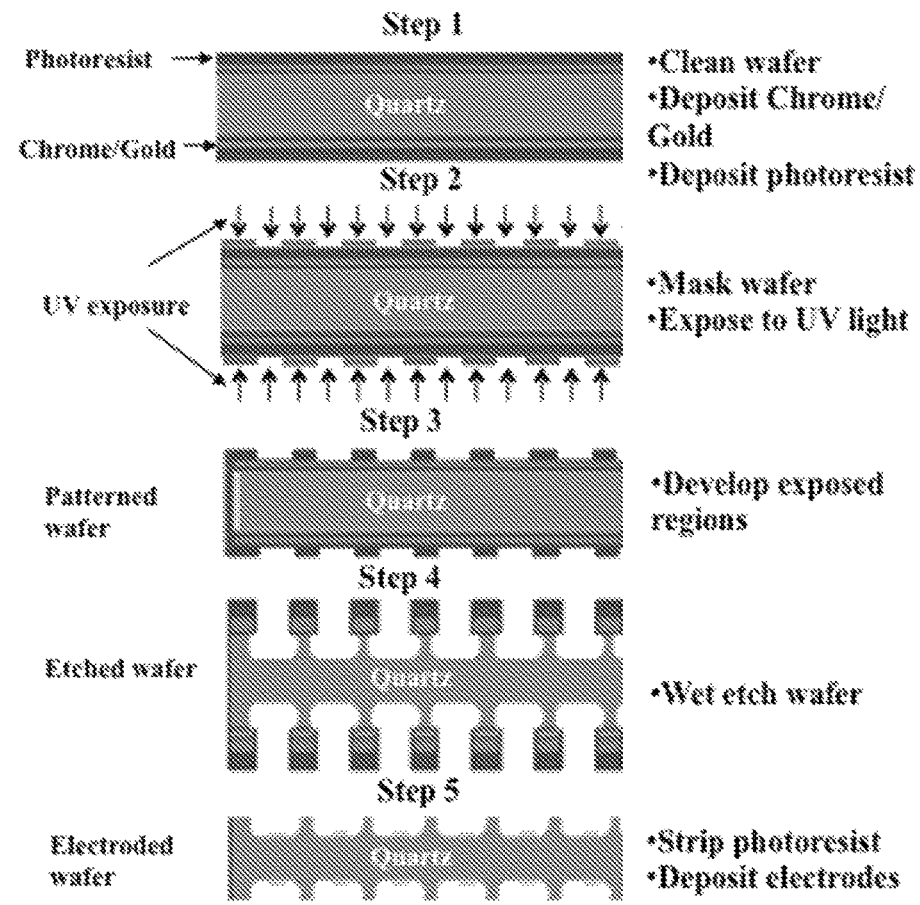
FIG. 10 is a schematic of the VHF biochip fabrication process.

An outline of the fabrication process for the VHF biochips 102 is shown in FIG. 10. This process employs high quality, double lapped quartz wafers 118. Wafers 118 are first cleaned and plated with a thin layer of chrome/gold. Next the gold is coated with photoresist which is then shielded (in the desired pattern) with a transparency/metal mask and exposed to UV light that cures/dissolves the photoresist (depending if it is a positive or negative photoresist). After cleaning, the mask is removed and the gold layer is dissolved away in areas where the quartz 118 is to be etched. The exposed quartz 118 is then treated with a hydrofluoric acid solution that only etches the quartz 118. Knowing the etch rate, the sensors 114 can be etched to have the desired resonance frequency. Next the gold electrodes 120 are deposited and the VHF biochip 102 is ready to be used. Electrical traces 130, also of gold, are deposited on the top surface 126 and the bottom surface 128 of the substrate 118, as well as on the sidewalls of well 132 to connect with electrodes 120. In this illustration, the sidewalls of well 132 are vertical. However, the sidewalls of well 132 need not be vertical and uniform. Because of the anisotropic wet etch of quartz crystal, the etch rates along different crystal orientations may vary. For example, using a wet etch of quartz crystal using 10.9 mol/L hydrofluoric acid at 25° C., the etch rates for X, Y and Z axes are 0.02 μm/hour, less than 0.005 μm/hour and 9.6 μm/hour, respectively. This difference in etch rates results in non-uniform and non-vertical sidewalls of the well 132.

After the design of individual biosensors 114 is completed, other issues need to be considered in finalizing the layout of biochips 102. Biosensors 114 operate in thickness shear mode. These biosensors 114 have shear motions in the X-axis direction during operation. If two biosensors 114 are very close along the X-axis, mechanical coupling between the biosensors 114 may occur. This interference can result in a deterioration of the performance of biosensor 114, i.e. a reduced quality factor and lower sensitivity. Therefore, in the design of biochips 102, multiple biosensors 114 can be aligned along the Z-axis to minimize cross-talk between biosensors 114. Additionally, circular wells 132 around each biosensor 114 on the bottom of the chip act to mechanically isolate biosensors 114 from each other.

In order to design biochip 102, electrode and well sizes need to be optimized for improved mass sensitivity, quality factor, stability and signal-to-noise ratio.

Therefore a range of electrodes (0.3-1.5 mm) and well sizes (1-10 mm) were selected. Potential sizes are not limited to those shown herein. The sizes discussed below are specific to a 100 MHz resonant frequency biochip 114.

TABLE 1

Dimensions of the well and electrodes for a biochip with multiple wells and electrodes

| Sensor Thickness H (um) | Electrode Diameter D (mm) | Diameter to Sensor Thickness Ratio D/h | Etching Well Diameter W (mm) | Well Diameter to Electrode Diameter Ratio W/D |
|---|---|---|---|---|
| 16.671 | 0.305 | 18.3 | 3.048 | 10.0 | 1.524 | 5.0 |
| 16.671 | 0.406 | 24.4 | | 7.5 | | 3.8 |
| 16.671 | 0.508 | 30.5 | | 6.0 | | 3.0 |
| 16.671 | 0.762 | 45.7 | | 4.0 | | 2.0 |
| 16.671 | 1.016 | 60.9 | | 3.0 | | 1.5 |
| 16.671 | 1.270 | 76.2 | | 2.4 | | 1.2 |

The frequency of vibration of biochip 102 is determined by its thickness, h. For 100 MHz sensors, h=16.671 um. Keeping this height constant, a range of diameters D for electrodes 120 are selected. The diameters of electrodes 120 are chosen to provide a uniform electric field between electrodes 120. In general, D/h>20 is recommended to allow for strong electromechanical coupling and high quality factor. In order to determine the size of electrode 120, a biochip 102 having a range of D/h ratios from 18 to 76 was designed.

Also, the size of well 132 determines the mechanical boundary of the vibrating structure and can impact the performance of biochip 102 if improvidently chosen. It is also important to determine how much the well diameter can be reduced to reduce the sample volume on biochip 102. Therefore, two sizes for wells 132 were also designed.

Figure 11A:
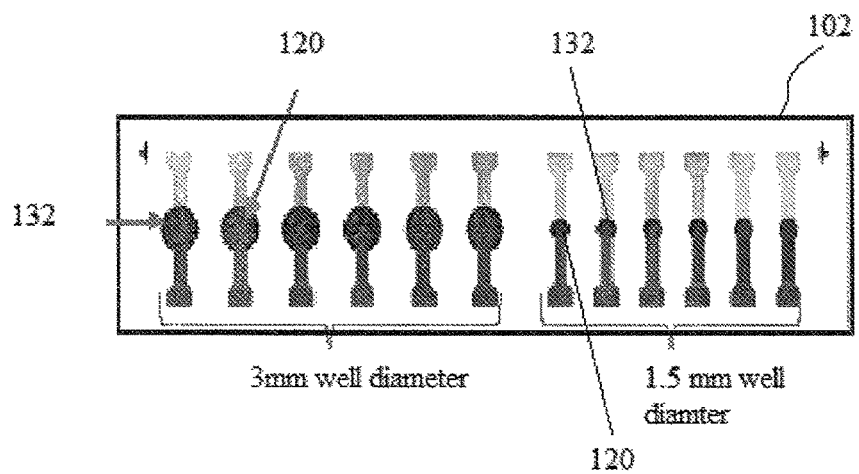
FIG. 11A shows the schematic of the multi electrode multi well VHF biochip.
Figure 11B:
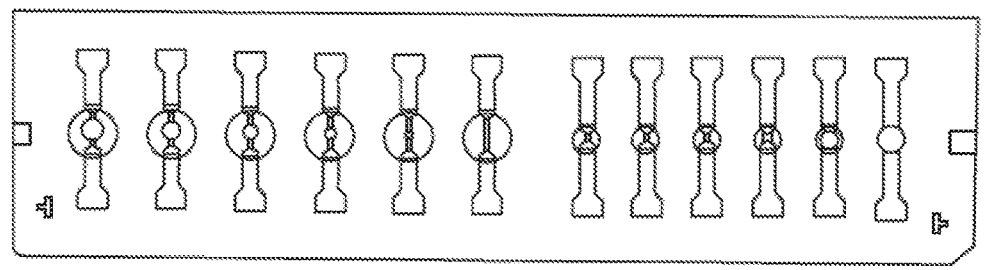
FIG. 11B shows the fabricated multi electrode multi well VHF biochip.

FIGS. 11A and 11B show a biochip 102 incorporating a range of electrode (0.3-1.5 mm) and well (1.5-3 mm) sizes. Based on these designs, etch masks and electrode masks necessary to fabricate biochip 102 were designed. Biochips 102 of FIGS. 11A and 11B were fabricated and tested.

Biochip 102 was connected to network analyzer 110 and tested for quality factor, resonant frequency, amplitude, phase, and noise in both unloaded (air) and loaded (DI water) conditions.

Figure 25:
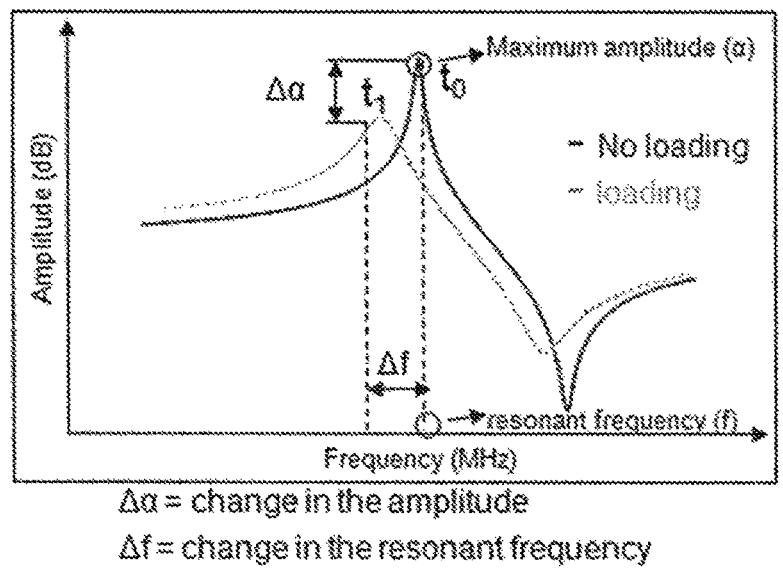
FIG. 25 shows measurements of $S_{21}$ of a VHF biosensor with and without loading.

The resonant frequency corresponds to the frequency at which the biosensor 102 vibrates with the maximum amplitude, FIG. 25. When loaded, the change in resonant frequency corresponds to the mass deposited on the surface of biosensor 102. The frequency is tracked corresponding to this amplitude during detection. It is therefore important to select the size of the electrode 120 and the well 132 that give the maximum frequency shift when loaded (i.e. the dimensions that have the highest mass sensitivity). A small amplitude change when loading is important as it indicates low losses and therefore lower noise. However this could also lead to low sensitivity to viscoelastic changes in liquids. Phase change closely correlates with the resonant frequency change. It is important from the point of view of the design of an oscillator based electronic measurement system as it will track zero phase.

Figure 12A:
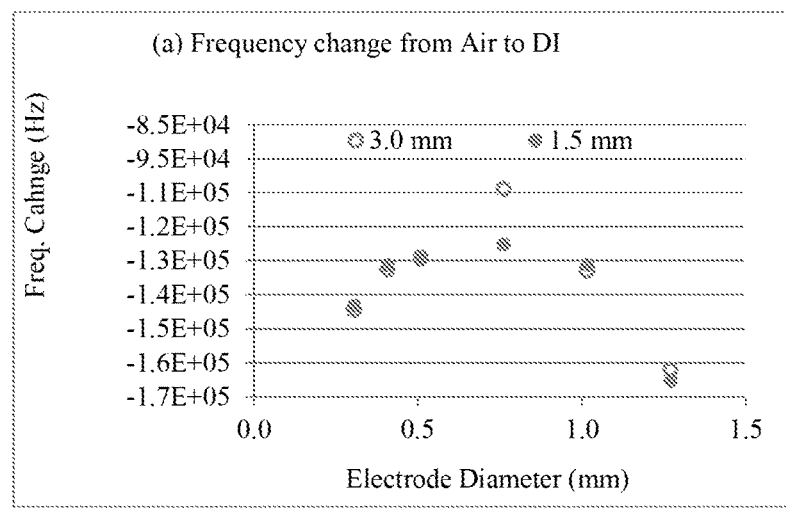
FIG. 12A is a graph of the frequency change from air to DI as a function of electrode and well diameter.
Figure 12B:
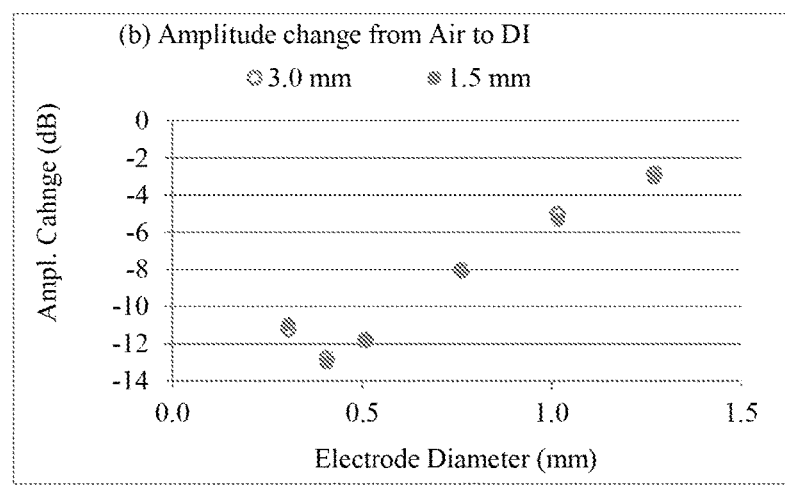
FIG. 12B is a graph of the amplitude change from air to DI as a function of electrode and well diameter.
Figure 12C:
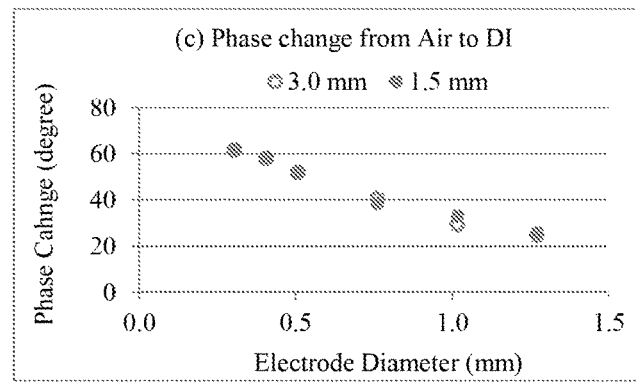
FIG. 12C is a graph of the phase change from air to DI as a function of electrode and well diameter.

FIGS. 12A, 12B, and 12C show the results. The change in resonant frequency, amplitude, and phase when the sensors are loaded with DI water is shown in these figures. As can be seen in FIG. 12A, the results show that there is a range of sizes of electrodes 120, namely, 0.5-0.8 mm that exhibits the highest sensitivity to mass loading.

Resonant amplitude is related to the losses at resonance. The choice of the diameter of electrode 120 plays a role in the observed losses at resonance. The aim is to have the lowest losses or damping under loaded conditions FIG. 12B shows the change in resonant amplitude when loaded with DI water. The losses decrease as the size of the electrode 120 increases. In the case of an amplitude change from air to DI, lower damping/losses are observed for larger diameters of electrodes 120.

The phase change of the VHF biochip 102 when loaded with DI water is shown in FIG. 12C. As can be seen, the phase is strongly depending on the electrode 120 diameters. Since the crystal oscillator works when the overall phase shift in the closed-loop is 0° or 360°, the phase of a VHF biosensor 114 has to be compensated for based on the design of the oscillator circuit. Therefore, FIG. 12C provides the data required for the successful operation of the oscillator.

Figure 13A:
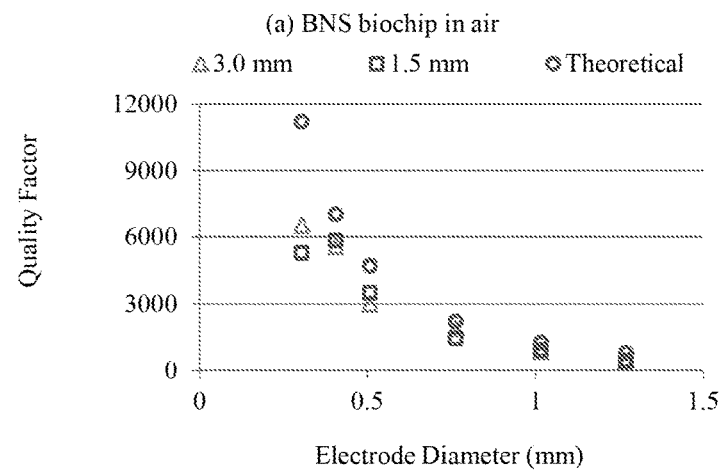
FIG. 13A is a graph of the quality factor of the VHF biochip as a function of electrode and well diameter in air.

The design parameters for the biochip 102 were the determined. As seen in FIG. 13A, in air, the Quality-factor (Q-factor) shows good correlation with theoretical expectations, indicating that the quality and fabrication of the biochips 102 meet the required standards. Utilizing the distribution of Q-factor of the biochip 102 when loaded with water (FIG. 13B), it was determined that a size of electrode 120 between 0.5 and 0.8 mm provides the highest Q-factor. This enables better curve-fitting and lower noise in frequency measurement. It was also shown that the maximum resonant frequency change from air to DI was observed for electrode diameter between 0.5 and 0.8 mm.

Figure 14A:
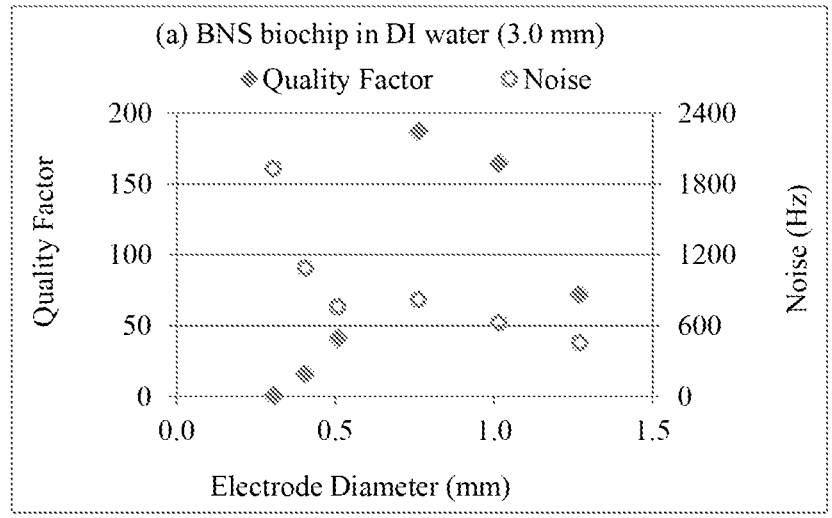
FIG. 14A is a graph of the quality factor and noise level of the VHF biochip as a function of electrode diameter for well size of 3 mm.
Figure 14B:
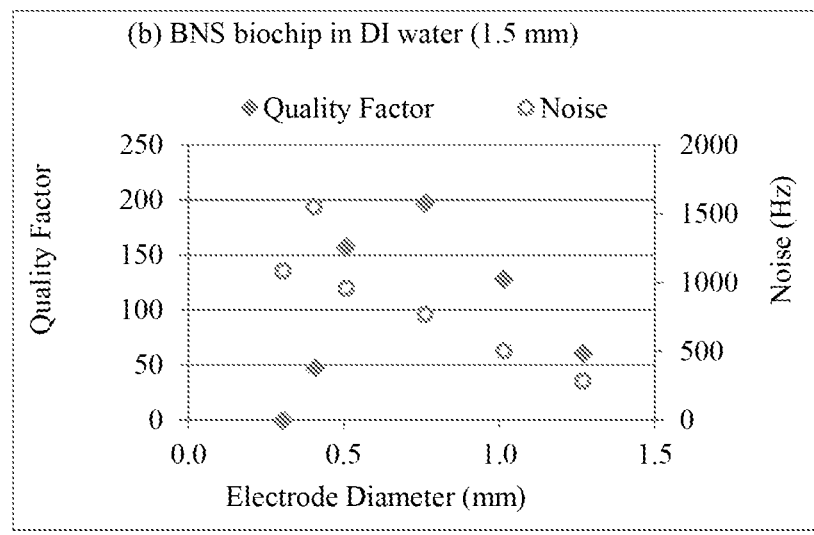
FIG. 14B is a graph of the quality factor and noise level of the VHF biochip as a function of electrode diameter for well size of 1.5 mm.

The noise level used in this study refers to the standard deviation of recorded resonant frequencies over a certain amount of time. This noise not only depends on the stability of VHF biosensors 114, but also the measurement technique used to acquire the resonant frequency. FIGS. 14A and 14B show the measured noise levels for 100 MHz VHF biosensors 114 in water. The results in FIGS. 14A and 14B show that the noise increases with decreased quality factor following theoretical expectations except for biosensors 102 with very large electrode diameters.

Taking the Q-factor, resonant frequency, phase, resonant amplitude, and noise into consideration, the VHF biochip 102 was designed to have an electrode diameter of 0.76 mm.

It was also shown that the diameter of the well 132 plays a minor role in the frequency change, amplitude change or phase change from air to DI water. Therefore, as the size of well 132 is reduced from 3:1, the ratio of the diameter of the well 132 to the diameter of the electrode 132 may be as low as 1.1-3:1.

The ability to reduce the size of well 132 allows for lower sample volume, less antigen loss, easier sensing of the fill up of well 132 and possibly increased sensitivity and detection kinetics. Also, the biosensor 114 with the smallest ratio of well diameter to electrode diameter (W/D) of 1.2 has the lowest noise level in DI water. Thus, well 132 preferably has a 1 mm diameter.

The quality factor (Q-factor) of biochip 102 is a ratio of the energy dissipated to the energy stored in an oscillating system. A high Q-factor result in low noise. Since the Q-factor is dependent on the diameters of the electrodes 120 and the wells 132, it can be optimized using biochip 102. Furthermore, the variation in quality factor with the dimensions of electrodes 120 and wells 132 changes under loaded conditions.

Figure 13B:
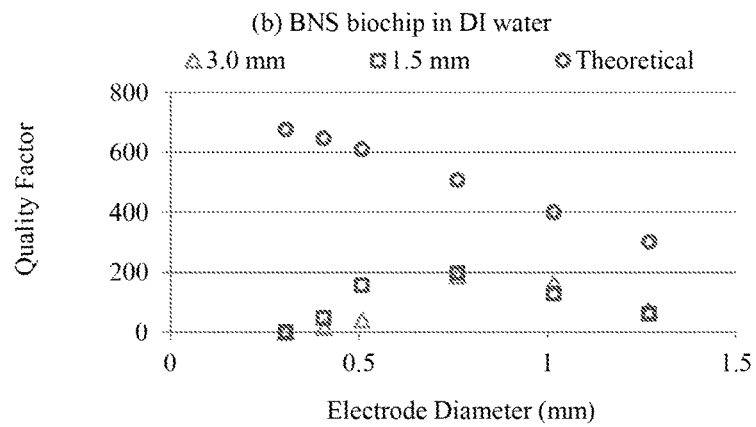
FIG. 13B is a graph of the quality factor of the VHF biochip as a function of electrode and well diameter in DI water.

FIGS. 13A and 13B represent the Q-factors in air and DI water. FIGS. 14A and 14B show the dependence of the quality factors of 100 MHz biochips 102 on electrode diameter. In air and DI water, the quality factors of 100 MHz biosensors 114 are independent of the well diameter (3.0 mm or 1.5 mm). In air, the measured quality factors are consistent with the theoretical values obtained from a transmission-line model except for biosensors 114 with the smallest diameter electrode 120.

The Q-factor follows a Gaussian distribution as the electrode size is increased. It has been determined that the 100 MHz biochip 102 should have a 0.5 to 0.8 mm diameter electrode 120 to provide the highest quality factor under loaded conditions. This approach can be extended to biosensors 114 having resonant frequencies ranging from 50-1000 MHz.

Based on the above study, refinements to the design parameters were determined.

TABLE 2

Design parameters for VHF Biochips

| Parameter | Typical | Unit |
|---|---|---|
| VHF Biosensor | | |
| Material | AT-cut quartz crystal | — |
| Frequency | 100 | MHz |
| Thickness of quartz membrane | 16.68 | μm |
| Diameter of gold electrode | 762 | μm |
| Ratio of electrode diameter to sensor thickness | 45.7 | — |
| Diameter of quartz membrane | 1.067 | mm |
| Ratio of membrane diameter to electrode diameter | 1.4 | — |
| Fluidic Channel between a Sensor and a Inlet/Outlet | | |
| Length | 3.810 | mm |
| Width | 0.406 | mm |
| Depth | 41.66 | μm |
| Fluidic Inlet/Outlet | | |
| Diameter | 1.524 | mm |
| Depth | 41.66 | μm |
| Orientation of Gold Electrical Traces (Top View) | | |
| On top surface of biochip | Z minor | — |
| On bottom surface of biochip | Z prime | — |
| Quartz Crystal Substrate | | |
| Length | 60.96 | mm |
| Width | 30.48 | mm |
| Depth | 100 | μm |

Figure 15:
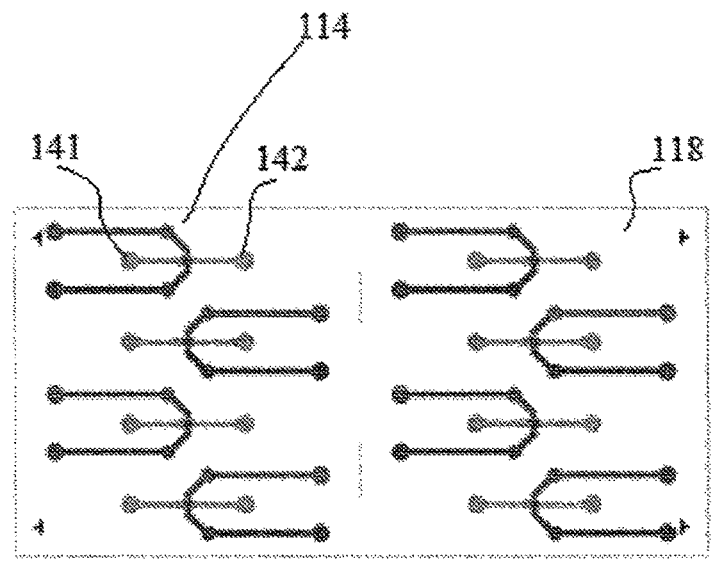
FIG. 15 is a top view of two VHF biochips designed on one quartz substrate.

The parameters listed in Table 2 were used to further refine the biochip 102. An alternative embodiment of biochip 102 was fabricated based on these design parameters and is shown in FIG. 15. FIG. 15 shows a transparent image of a 2.4"×1.2" quartz crystal substrate 118 on which two independent 100 MHz biochips were fabricated. Each biochip 102 comprises four biosensors 114.

Fluidic channels 117, inlets 141, and outlets 142 are designed on biochips 102 to provide pathways on biochip 102 for biological fluids, such as buffers, blocking agents, and samples, to biosensors 114. The physical dimensions of the fluidic channels 117, inlets 141 and outlets 142 are selected based on the following considerations. The fluidic channels 117 should allow efficient delivery of biological fluids to improve the sensitivity of biosensors 114. The fluidic channels 117 preferably allow smooth fluid flow to reduce noise. Inlets 141 and outlets 142 preferably allow reliable sealing of fluids and easy connection with an external fluid delivery or removal system. The length (5-20 mm), width (0.1-2 mm), and depth (22-50 μm) of the fluidic channels 117 are preferably as small as possible in order to reduce the size of biosensor 114 and the fluid volume (preferably 10-1000 nL) on the biochip 102, while not significantly increasing the complexity in the development of enclosure 104.

In the current design of biochips 102, fluidic channel 117 between biosensor 114, inlet 141 and outlet 142 has dimensions of 3.810×0.406×0.041 mm (L×W×D). The diameter of inlet 141 and outlet are each 1.524 mm.

A biochip 102 comprises multiple biosensors 114 that have an electrode 120 on each of top surface 126 and bottom surface 128. Gold electrical traces 130 on the biochip 102 provide electrical connections between individual biosensors 114 and an external electrical measurement system. Traces 130 are commonly routed from electrodes 120 on biosensors 114 to electrical pads 131 located at the edges of biochip 102. During this routing, electrical traces 130 with shorter lengths are preferred in order to reduce stray capacitance and trace-resistance and improve the quality factor to preferably 500-10000. Electrical traces 130 may cross fluidic channels 117, if a shorter length of electrical traces 130 is the only limiting factor.

When an electrical trace 130 crosses through the bottom of a fluidic channel 117, biological molecules flowing inside fluidic channel 117 may bind to the electrical trace 130 if it is not fully blocked. This may reduce the effective concentration of biological molecules, inside the fluidic channel 117 and result in an inaccurate measurement. Therefore, in the design of biochip 102, it is preferred to avoid traces 130 crossing fluidic channels 117 and therefore the shortest path outside of the fluidic channel 117 is selected.

The size of quartz crystal substrate 118 may be about 2.4"×1.2"×0.004" for the biochip 102 of the invention. However, it should be understood that other sizes may be selected depending on the biochip 102 desired. In practice the size of the substrate 118 is selected to be within the current processing capability of biochip fabrication.

The invention was demonstrated with a 100 MHz biochip 102 for detection of 10-1500 ng/mL of AFP in human serum. The biochip 102, shown in FIG. 19, is 25×25 mm in order to provide easy handling. Based on the test results, this biochip 102 can be reduced to $\frac{1}{5}^{th}$ its size when an automated approach in handling and functionalizing is employed. Similarly, fluidic channels 117 and electrical traces 130 can all be reduced in size allowing for the fabrication of a large number of inexpensive biochips 102 using standard semiconductor wet machining techniques.

In FIG. 15, each area indicates the top side of a biosensor 114, including two circular regions at the two ends of inlet 141 and outlet 142, and a smaller circular region in the center, forming the top half of the inverted mesa structure. This circular region is etched during the biochip fabrication process. The bottom half of the inverted mesa structure is not visible in this figure.

A schematic of the fabrication steps involved in the design of a biochip 102 is provided in FIG. 10. First, the size and orientations of substrate 118 is determined and the material is selected. In this embodiment, the material is quartz crystal. Then, the resonant frequency for biochip 102 is determined depending upon the application. The height or thickness of the membrane 122 corresponding to the selected resonant frequency is determined. Then, the ratio of the diameter of electrode 120 to the diameter of membrane 122 is determined. This is then used to choose a diameter of electrode 120. Once the electrode diameter is chosen, a corresponding diameter of membrane 122 is calculated.

Then, the arrangement of biosensors 114 on a chip is determined. For example, each biosensor 114 may be provided with individual fluidic channels 117, inlets 141 and outlets 142 or multiple biosensors 114 may be connected in series or parallel sharing fluidic channels 117, inlets 141 and outlets 142. The inlet and outlet diameters and the dimensions of fluidic channels 117 are then determined. The layout of biochips 102 on the substrate 118 may then be designed using, for example, a CAD program. Electrical contact pads 121 for an external measurement system are then provided. Electrical traces 130 are routed between individual biosensors 114 and corresponding electrical contact pads 121 while avoiding crossing of traces 130 and fluidic channels 117. The individual layers are then patterned in the CAD system including the top etch layer, top electrode layer, bottom etch layer and bottom electrode layer.

Biochips 102 are fabricated on a substrate 118, preferably AT-cut quartz. During the fabrication of biochip 102, photomasks are needed in the etching and plating processes. Upon completion of the design of biochip 102, the photomasks may be designed in CAD software to prepare for photomask fabrication.

There are two types of photomask that are required for fabrication of biochips 102. Etch masks for quartz etching to develop inverted mesa structures for biosensors 114 and plating masks for electrode plating. These masks enable etching of the substrate 118 to create an inverted mesa structure and formation of designed patterns of electrodes 120.

Figure 17A:
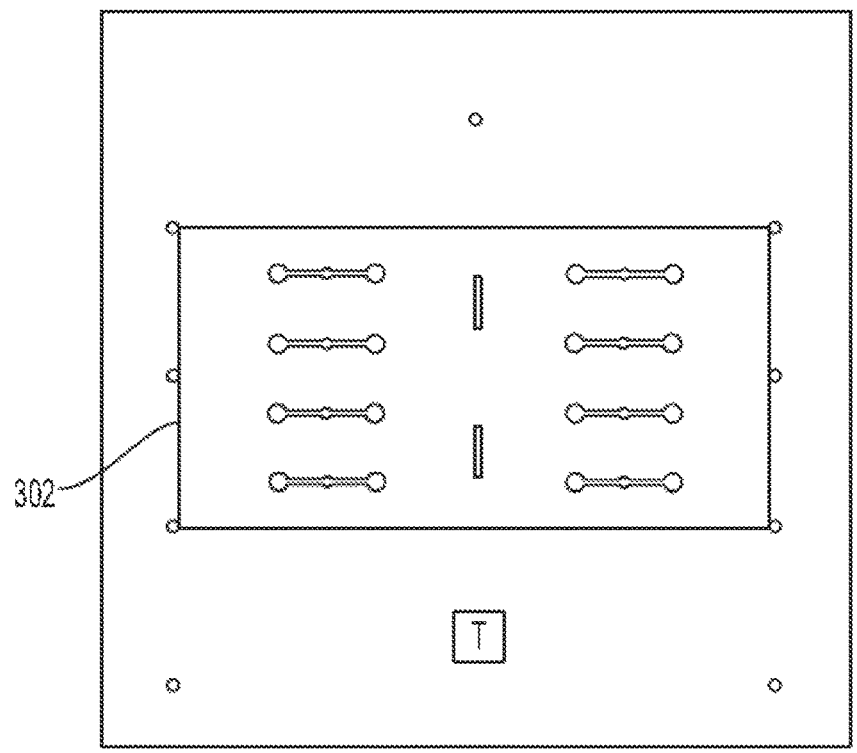
FIG. 17A shows a top etch mask for a VHF biochip.
Figure 17B:
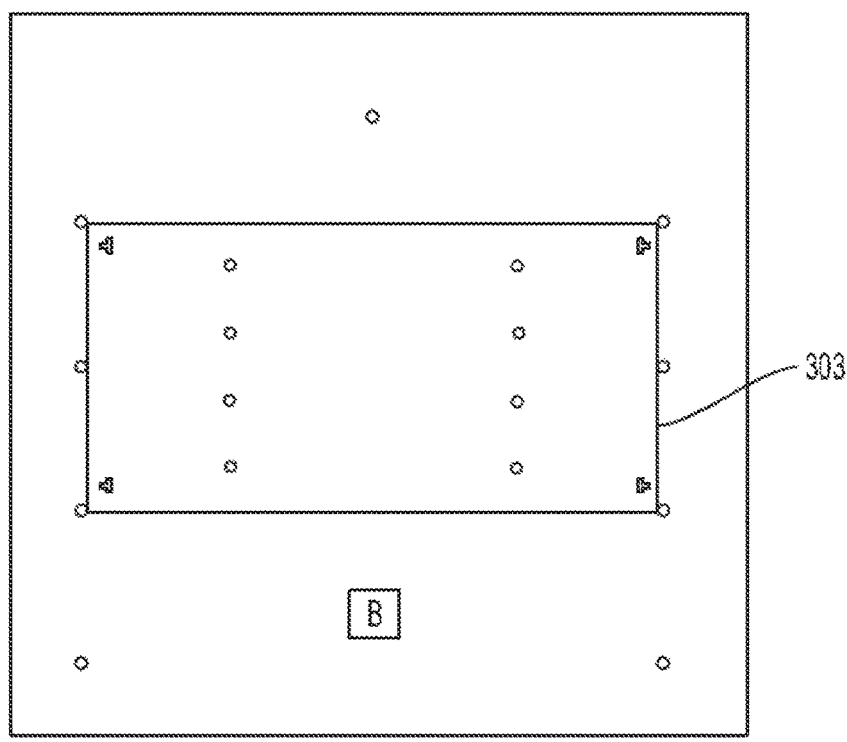
FIG. 17B shows a bottom etch mask for a VHF biochip.

Biochips 102 may utilize an inverted mesa structure to simultaneously achieve a high sensitivity and strong mechanical stability for medical applications. FIGS. 8B, 9A, and 9B show the inverted mesa structure. The top side of a VHF biochip 102 incorporates half of the inverted mesa structure and fluidic channels 117 for flowing biologically relevant fluids through biosensors 114, while the bottom side of a VHF biochip 102 consists of the other half of the inverted mesa structure. In order to reduce the time and cost of fabrication, the etching process may employ double-sided etching to reduce the etching time by half compared with single-sided etching. The double-sided etching process requires two independent etch masks: a top etch mask, an example of which is shown in FIG. 17A, and a bottom etch mask, an example of which is shown in FIG. 17B.

The plating process is used to deposit metal electrodes 120 on biochip 102. The substrate 118 is passed through a plating process after it is etched. Since each biosensor 114 requires two terminals, one each on opposite surfaces of biochip 102, a pair of plating masks, namely, a top plating mask and a bottom plating mask, examples of which are shown FIGS. 18A and 18B, may be used for the fabrication.

There are different techniques and processes that can be used to fabricate biochips 102. Once a specific fabrication process is selected, three aspects need to be considered in the design of photomasks: the type of photoresist, e.g. positive resist or negative resist, the emulsion side, e.g. emulsion side up or emulsion side down, and the polarity, e.g. a positive mask or negative mask. In the fabrication of biochips 102, positive resist, emulsion down and positive photomasks are the preferred selections.

For a photomask, the emulsion side is the image surface on a transparency film. There are two types of emulsion for a photomask emulsion up and emulsion down. An emulsion up photomask has the emulsion or image surface facing toward a viewer when the mask is viewed so that the text or design is right reading. In other words, the emulsion is on the top side of a photomask and has the same pattern as the designed biochip 102. An emulsion down photomask has the image surface facing away from a viewer when the mask is viewed so that the text or design is right reading. In the current design and fabrication of photomasks for VHF biochips, emulsion down masks are chosen for both the etch masks and plating masks.

Etch and plating masks are printed on transparency films or metal substrates, with patterns of black/dark and clear areas depending on the mask design. The black/dark area on a photomask prevents light from going through, while the clear area allows light to go through. There are two opposite polarities for photomasks: positive mask and negative mask. For a positive photomask, the black area in the CAD design will be black on the mask and the clear area in the design will be clear on the mask. For a negative photomask, the black area in the CAD design will be clear on the mask and vice versa. In the current design and fabrication of photomask for the biochips 102, a positive photomask is chosen.

To initiate the design of photomasks for biochips 102, two requirements have to be satisfied, the design of biochip 102 must be complete and the type of photoresist, type of emulsion and polarity of mask must be selected. One embodiment of a biochip 102 is shown in FIG. 15. This is a top-view, transparent image of a 2.4"×1.2" substrate 118, which can be quartz crystal, on which two independent 100 MHz biochips 102 are fabricated. Each biochip 102 can comprise four biosensors 114. However, it should be understood that more biosensors 114 can be used.

Figure 16:
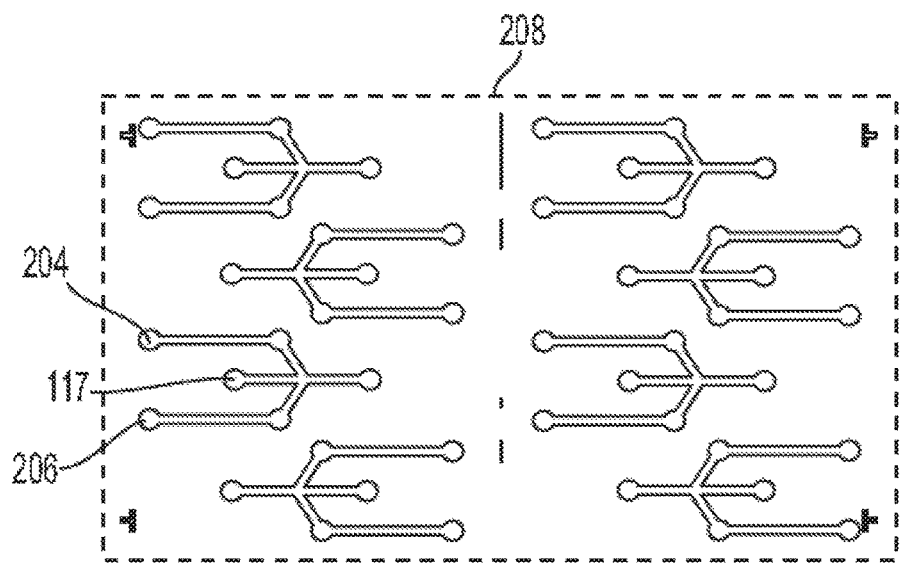
FIG. 16 shows a top view of a quartz crystal substrate/disc comprising two biochips.

In FIG. 16, the top of substrate 118, is etched in regions 117 during the fabrication of VHF biochip 102. Top region 204 and bottom region 206 indicate the locations of top and bottom electrodes 120 for biosensors 114, respectively. The two vertical regions 208 in the center of biochip 102 will be used as guide lines to dice the substrate into two parts. After substrate 118 is fully processed, it will be cut along the two vertical regions 208 to obtain two separate VHF biochips 102.

The top of biochip substrate 118 consists of multiple etch regions 117 each comprising a biosensor 114 at the center, a fluidic inlet 141 and a fluidic outlet 142 at the two ends, and fluidic channels 117 connecting the inlet 141 and outlet 142. The etched regions on the bottom of substrate 118 are not visible in this top view. The bottom etch regions differ from the top etch regions 117 in that they only consist of areas (or wells) for etching of biosensors 114, without fluidic channels 117, fluidic inlets 141 or fluidic outlets 142. Both the top and the bottom of the biochip are preferably etched simultaneously.

During fabrication of biochip 102, a substrate 118 preferably made of quartz crystal is coated with a layer of positive resist. Based on the design of the biochip 102 shown in FIG. 15 and the design considerations discussed above, the top and bottom etch masks for the current VHF biochips are designed, as shown in FIGS. 17A and 17B.

The etch masks for biochips 102 are fabricated on transparency films. Both top and bottom etch masks have dimensions of 3"×3". The dimensions of the black area on the two masks are 2.4"×1.2", the same size as substrate 118.

It can be seen that the middle area of the top etch mask shown in FIG. 17A is the same as the top etch region 117 shown in FIG. 16. This is because the top etch regions 117 in the biochip design indicate the locations that need to be etched to create the inverted mesa structure for biosensors 114, and the middle areas 302 on the top etch mask indicate the areas where positive resist will be exposed and dissolved in the photoresist developer, and where the quartz crystal will be etched. Similarly, the second middle areas 303 on the bottom etch mask, shown in 17B, indicate the areas on the bottom surface of the quartz crystal substrate/disc that will be etched.

In the plating process, substrate 118 is first deposited with a gold thin layer. Then, it is coated with a layer of positive resist. A plating mask is placed on top of the photoresist. After light is applied, the clear areas on a plating mask indicate the regions where the positive resist will be exposed and dissolved in the photoresist developer, and where the gold thin layer will be dissolved in gold etchant. FIGS. 18A and 18B show the top and bottom plating masks for an embodiment of the invention.

Both of the top and bottom plating masks are also fabricated on transparency films and have dimensions of 3"×3". The rectangular white area on each mask has the same size as the quartz crystal substrate/disc, namely, 2.4"× 1.2".

The traces 130 on the top plating mask shown in FIG. 18A have exactly the same pattern as the top region 204 areas shown in FIG. 16, corresponding to top electrodes 120. To create the pattern of electrodes 120 as the top etch region 117, the gold layer in these regions needs to be protected from gold etching. Since a positive resist is used, the corresponding regions on the plating mask must be black. There is a little difference in the bottom plating mask, on which the black traces, shown in FIG. 18B, are the mirror image about the Z' axis of the bottom region 206 shown in FIG. 16. This is because FIG. 16 is a see through view of biochips 102 and an emulsion down mask is selected.

In FIG. 16, top etch regions 117 indicate regions of quartz crystal to be etched away and top region 204 indicates regions of gold layer to retain. This results in the different background of the 2.4"×1.2" areas, corresponding to the quartz crystal substrate, on etch and plating masks, black for etch masks and white for plating masks.

In the fabrication of biochips 102, photomasks made of transparent films or metal may be used.

The procedure for the fabrication of the biochip 102 involves multiple steps which have been listed in Table 3.

TABLE 3

| Step | Description |
| --- | --- |
| Optical Characterization of wafers | the quality of the quartz blanks are characterized surface roughness using optical methods like SEM and AFM. |
| Wafer cleaning followed by drying | Cleaning protocols are used to rid the wafers of organic, metallic and oxide contaminants. The cleaned wafers may be dried by a soft bake. |
| One-side Chrome Deposition | A thin layer of chrome about 50 nm thick is thermally evaporated onto one face of the quartz wafer so as to make it opaque. Cleaning protocols are to be followed after depositing the chrome. |
| Spin Coating HDMS Primer | On the top face (the one without chrome layer) of the wafer, spin coat a layer of the primer Hexamethyldisilazane (HDMS) and bake. Primer HDMS serves as an adhesion promoter for the photoresist. |
| Spin coat Photoresist | On the top face of the wafer, spin coat a layer of positive photoresist Shipley 1827 and bake. |

All of the above steps were implemented and shown to work.

Etching and electrode masks were designed and fabricated according to the specifications in Table 2. These were then used to fabricate biochip 102 as shown in FIG. 19. All four biosensors 114 on biochip 102 were tested using a network analyzer 110. The $S_{21}$ scattering parameters of the biochip 102 are plotted in FIG. 20.

Figure 20:
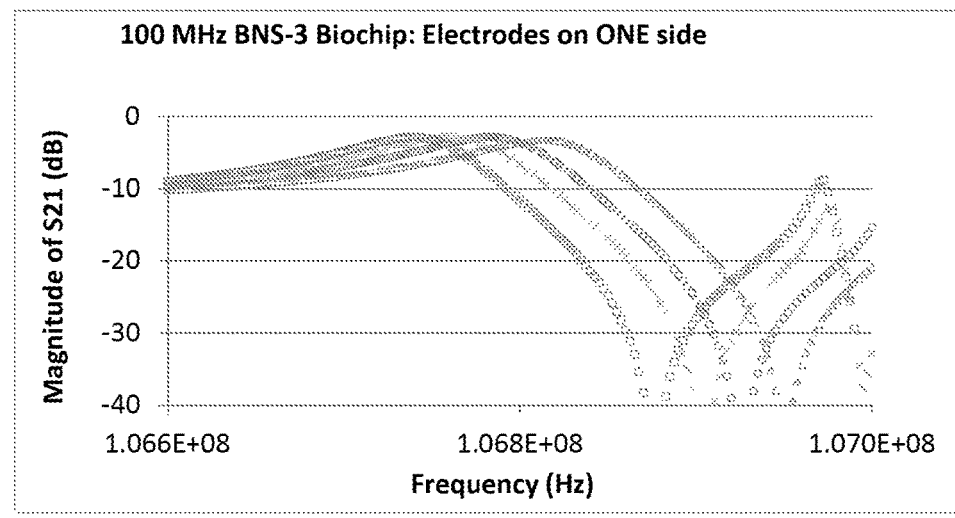
FIG. 20 shows the forward transmission coefficient ($S_{21}$) for the four sensors of the biochip demonstrating that all 4 sensors have close to an identical response. They are intentionally shifted from each other for better viewing.

As can be seen from FIG. 20, all four biosensors 114 have nearly identical performance. The biosensors 114 meet expectations in terms of Q-factor and resonant frequency and amplitude.

Next the enclosure 104 for biochips 102 is designed. In order to detect biomarkers, such as AFP, the VHF biochip technology is utilized to fabricate a VHF measurement system 100. This system 100 has three major components: biochip 102, enclosure 104 and measurement electronics 150. Biochip 102 is the sensing element that enables the detection of biomarkers. Enclosure 104 provides reliable mechanical protection, fluidic delivery and electrical connections and delivers fluidic buffers and samples to biochip 102, with the help of the pump 106, which may be a peristaltic pump, and necessary fluid connections. Measurement electronics 150 provide continuous monitoring of the responses of biosensors 114. A standard lab-based VHF biochip system 100 includes an enclosure 104 with a biochip 102 enclosed inside, a pump 106 for delivering buffers and samples to biochip 102, and a network analyzer 110 for determining the parameters of biosensors 114. Network analyzer 110 can be replaced by oscillator-based electronics in a bench-top VHF biochip system 100.

An embodiment of enclosure 104 may include two PDMS layers. The bottom PDMS layer provides mechanical support for the biochip 102. The top PDMS layer ensures proper sealing of the on-chip fluidic channels 117 on the biochip 102. This top layer also has built-in fluidic channels 117 for connecting the fluidic inlets 141 and fluidic outlets 142 on the biochip 102 to the outside pump 106. This enclosure 104 has been used in the successful detection of AFP and generation of a standard curve.

Biochip 102 may be functionalized on a Petri dish with the top side of the chip facing up. Each fluidic channel 117 is cleaned. 1 µl of anti-AFP antibody is added to the sensing region of fluidic channels 117 (in this case, Genway 57) at concentration of 1-200 µg/ml to cover the entire sensing region of electrodes 120. The biochip remains at about 20° C. for about 30 minutes or until the liquid dries. Molecular-grade H$_2$O is added in a sufficient amount to cover the spot size formed by the Genway57. The H$_2$O removed by vacuum and the washing process is repeated two more times or until all fluidic channels 117 have been washed with molecular-grade H$_2$O To a cleaned PDMS section of enclosure 104 is added a cleaned biochip 102 on a fiber free sheet of paper. Fluidic inlets 141 and fluidic outlets 142 are cleaned and the PDMS is gently lowered PDMS onto biochip 102. The PDMS adheres well to substrate 118 and will form a good seal of fluidic channels 117. Electrical tabs 121 to which the electrical traces 130 are attached fall within the grooves on the PDMS.

The PDMS and biochip 102 are attached to the lower layer of polymethyl methacrylate (PMMA), such that the electrical tabs with glued wires (on the back side of the chip) fall into the grooves. If the PMMA is clean the PDMS will adhere to lower PMMA and stay in place. Using thin strips of scotch tape, the wires are taped to the PMMA plate. A thin plastic sheet (could be a transparency) is cut to the size of the PDMS and placed on the top of the PDMS prior to placing the top PMMA. This is important to prevent the PDMS from adhering to the top PMMA. Top PMMA is then attached to bottom PMMA and enclosure 104 with, for example, screws.

Enclosure 104 is screwed into the base plate and connectors are attached to the gold wires. The wires are taped to the PMMA base plate allowing for slack in the wires. The setup is now ready for experimental testing.

The electrical connections to the biosensors 114 were made by utilizing silver paint and UV glue to attach gold plated thin wires (60 um diameter Tungsten wire with 1.5 um gold coating) to the pads of the electrodes 120. This setup has worked successfully for 100 MHz biochips 102. However, the thin and long metal wire connections may cause serious deterioration in the performance of biochips 102 that operate at higher resonant frequencies, such as at least 200 to 300 MHz.

Figure 21:
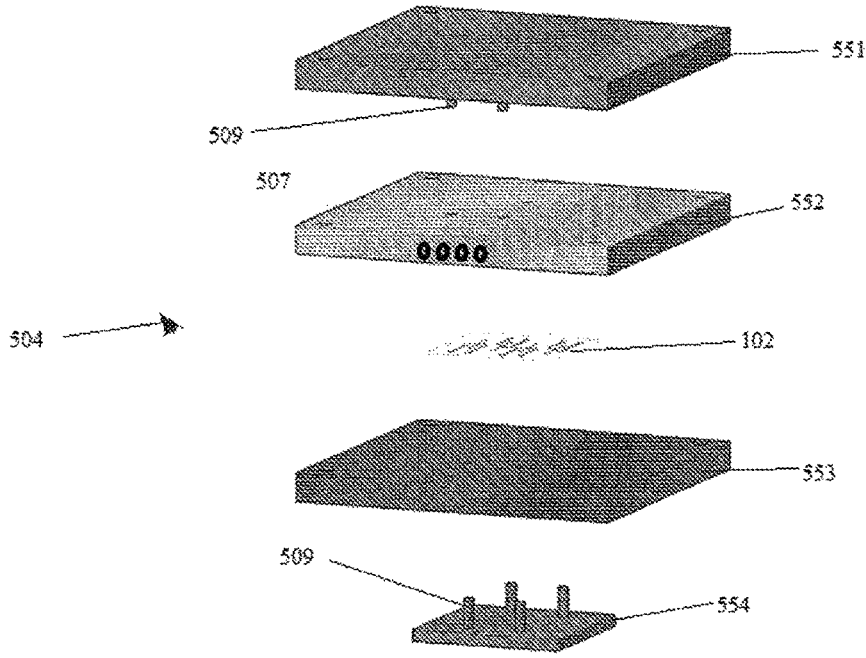
FIG. 21 is a diagram of the designs of VHF biochip enclosure with sample delivery from the side of the enclosure.

An improved design for an enclosure 504 is shown in FIG. 21. The new enclosure 504 utilizes pogo pins 509 to make electrical connections to biochips 102, instead of thin metal wire and silver paint/UV glue. This reduces the resistance and inductance associated with thin, long metal wires, and improves the quality factor and the detection limit of the system. These connections may be replaced by wire bonding the traces 130 to PCB's.

Enclosure 504 includes a PDMS layer 551 to provide mechanical protection and fluidic channels 117 for the four pairs of fluidic inlets 141 and fluidic outlets 142. Top PMMA layer 552 protects biochip 102 and supports pogo pins 509 for electrical connections to electrodes 120 on the top side. Bottom PMMA layer 553 protects biochip 102. Bottom electrical layer 554 supports pogo pins 509 for electrical connections to electrodes 120 on the bottom side.

Four pairs of pogo pins 509 provide reliable electrical connections to the sealed biochip 102. RF cables (RG 174): provide electrical connections between pogo pins 509 and a network analyzer 100, which may be an external instrument (Agilent 4395A Network Analyzer).

To assemble enclosure 504, a clean biochip 102, PDMS layer 551, PDMS backing layer, top PMMA layer 552 and bottom PMMA layer 553 are provided. Biochips 102 are attached to PDMS layer 551 with proper alignment of fluidic channels 117 and electrical connections. PDMS backing layer is then attached to PDMS layer 551.

Figure 22:
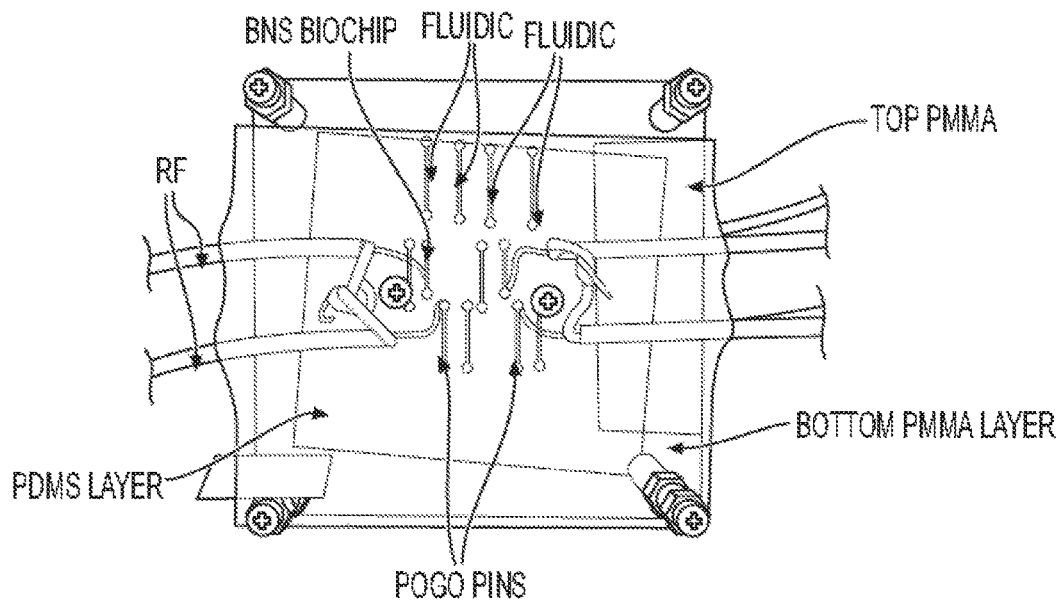
FIG. 22 is an image of the fabricated VHF biochip enclosure shown in FIG. 21.

Assembled PDMS layer 551 is located on bottom PMMA layer 553 and biochip 102 is aligned with the holes 507 for pogo pins 509. Top PDMS layer 551 is added and the four pogo pins 509 are aligned and fixed to top PDMS layer 551 with electrodes 120 on biochip 102. The whole assembly is fastened with four machine screws and nuts at the four corners, as shown in FIG. 22

Figure 23:
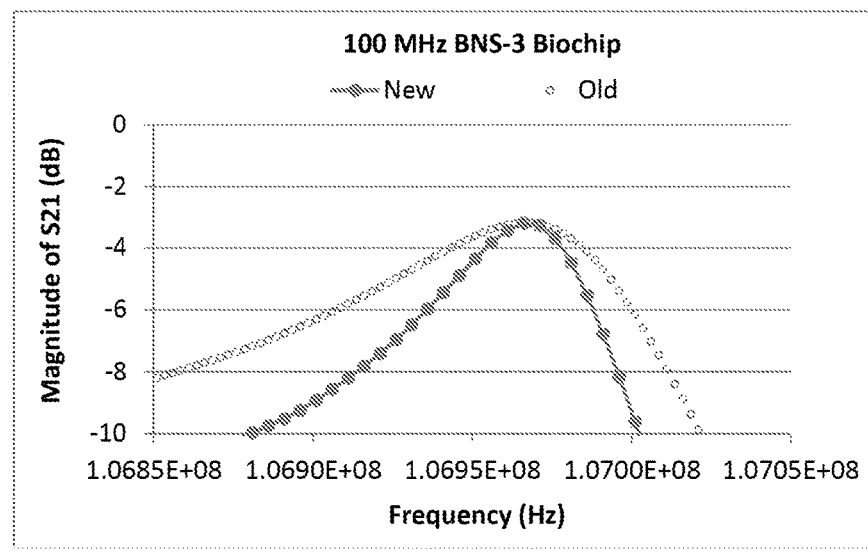
FIG. 23 is a graph showing that the quality factor of the resonant curve is improved from 1000 to 1900 by reduced electrical trace length using enclosure showing in FIG. 21.

Enclosure 504 was tested to evaluate its performance in comparison to enclosure 104. FIG. 23 shows a comparison of the responses of the same 100 MHz biochip 102, when located in enclosure 504. FIG. 23 also shows that the response of the 100 MHz biochip 102 has a much sharper peak when encapsulated in enclosure 504 when compared with enclosure 104. This difference in peak sharpness is indicated by the quality factors given in Table 4.

TABLE 4

| Biochip Encapsulation | Quality Factor |
| --- | --- |
| Encapsulated in enclosure 104 | 1090 |
| Encapsulated in enclosure 504 | 1954 |

Table 4 shows that the quality factor of the 100 MHz biochip 102, in the enclosure 504 is close to double that of the same biochip 102 in enclosure 104. This improvement in the quality factor results in a reduced noise level and thus an enhanced signal-to-noise ratio and an improved detection limit for VHF biochip system 100.

Figure 24:
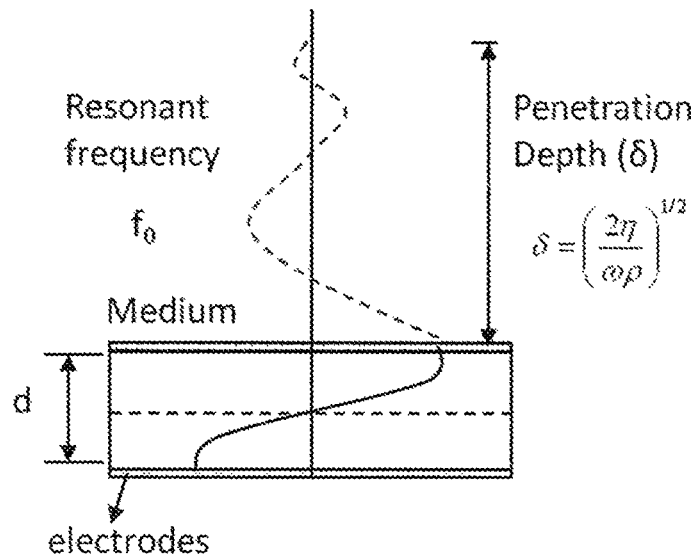
FIG. 24 shows the thickness shear motion of a biosensor.

The operation of the biochip 102 is based on biosensors 114, which are bulk acoustic wave (BAW) sensors excited in a thickness shear mode (TSM) of vibration. Each biosensor 114 behaves like a high quality mechanical resonator, which can be characterized by its impedance, admittance, forward transmission coefficient ($S_{21}$) or other parameters. A TSM sensor is very sensitive to changes in physical properties, such as density and viscosity, of the medium in contact with the TSM sensor. Biosensors 114 can be used in biomedical applications that involve changes in physical properties inside a medium. When an alternating electrical signal is applied to the top and bottom electrodes 120 of a biosensor 114, a plane acoustic wave is generated inside the biosensor 114, and the sensor exhibits shear displacements with maximum amplitudes reached at the top and bottom surfaces, as shown in FIG. 24.

The resonant frequency, $f_r$, of this shear acoustic wave is determined by the sensor thickness and the velocity of the shear wave inside the sensor, as given by equation 5.

$$f_r = \frac{v_q}{2 \cdot t_q} \quad (5)$$

where, $v_q$ is the shear acoustic velocity in the biosensor 114; and $t_q$ is the thickness of the biosensor 114. This shear acoustic wave can penetrate into the medium that is in contact with the biosensor, as illustrated in FIG. 25. This wave decays exponentially with a decay constant 6, as given in Eq. 6.

$$\delta = \left(\frac{2\mu}{\omega_r \cdot \rho}\right)^{\frac{1}{2}} \quad (6)$$

where, $\delta$ is called penetration depth; $\mu$ is the dynamic viscosity of the medium; $\omega_r$ is the angular frequency of fr and $\omega_r = 2\pi \cdot fr$; and $\rho$ is the mass density of the medium.

Since the acoustic wave decays exponentially in proportion to the penetration depth, the amplitude and phase of this wave are very sensitive to changes in the viscosity and density of the medium. Due to the acoustic coupling between this wave and the shear wave inside biosensor 114, the frequency, amplitude, and phase, can be monitored to measure the changes in the viscosity and density of the medium within the penetration depth.

Common parameters used to monitor the performance of a biosensor 114 are impedance, admittance, and forward transmission coefficient ($S_{21}$). These parameters are vectors and can be converted to each other under certain conditions. In the development of biochips 102, $S_{21}$ is chosen for the measurement of biosensors 114. FIG. 25 shows a typical change in $S_{21}$ of a biosensor 114 with and without loading.

In this figure, the curves are the dependence of the amplitude, in dB, of $S_{21}$ on frequency when biosensor 114 is not loaded and loaded, respectively. The frequency corresponding to the maximum amplitude is the resonant frequency of the biosensor 114. It can be seen that the resonant frequency of a loaded biosensor 114 shifts leftwards or decreases. The maximum amplitude of a loaded biosensor 114 is also lower than that of an unloaded biosensor 114. These changes in frequency and amplitude are caused by loading of biosensor 114, such as by immobilization of proteins or binding of antigens with immobilized antibodies, etc. $\Delta f$ and $\Delta \alpha$, can be correlated with the amount of additional mass loaded on the sensor, which, in turn, relates to the concentrations of biological molecules in the medium.

Figure 26:
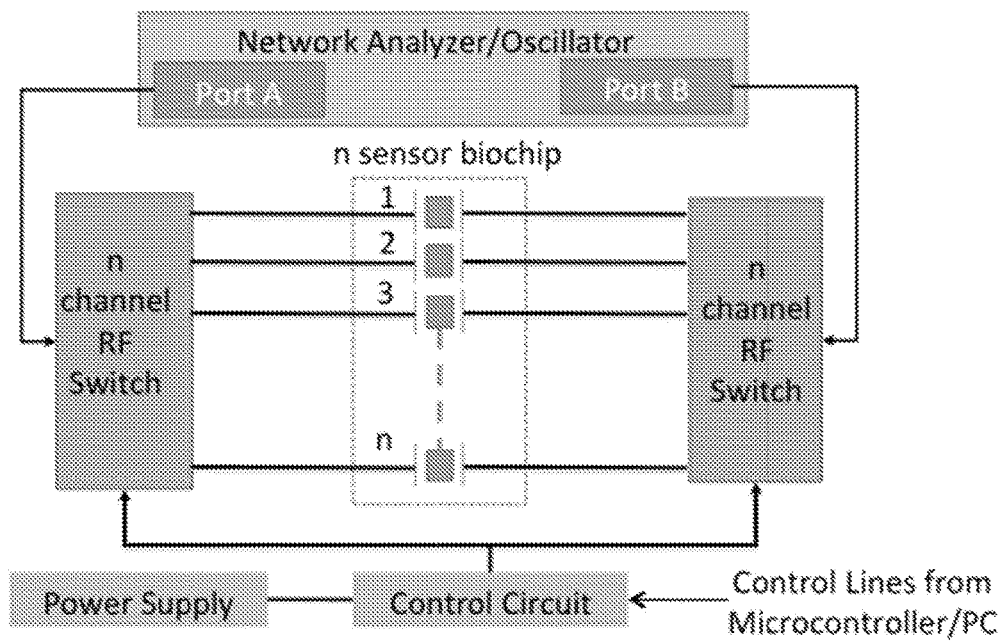
FIG. 26 is a schematic of the electrical excitation of an n-sensor VHF biochip using a network analyzer or oscillator-based measurement system and an RF switch.

A schematic of an n-channel electronic measurement system is shown in FIG. 26. The measurement electronics for biochips 102 are a network analyzer 104, such as an Agilent 4395A, which may be used to measure the forward transmission coefficient, $S_{21}$, of biosensors 114. A custom control program is installed on a computer 112 to control network analyzer 104 to measure parameters of biosensor 114. A 4-channel (or higher, i.e. n-channel) RF switch 104 is used to measure biosensors 114 on one biochip 102.

To set up the electrical measurement system, the following protocol should be followed: verify that hardware devices are well connected through cables, connect network analyzer 110 to computer 112 via a GPIB cable, connect network analyzer 110 to RF switch 108 via SMA cables, connect RF switch 108 to computer 112 via a parallel cable, and connect the RF switch 108 to a biochip 102 via SMA cables. The control program is set up according to the frequency of biochip 102

Figure 30:
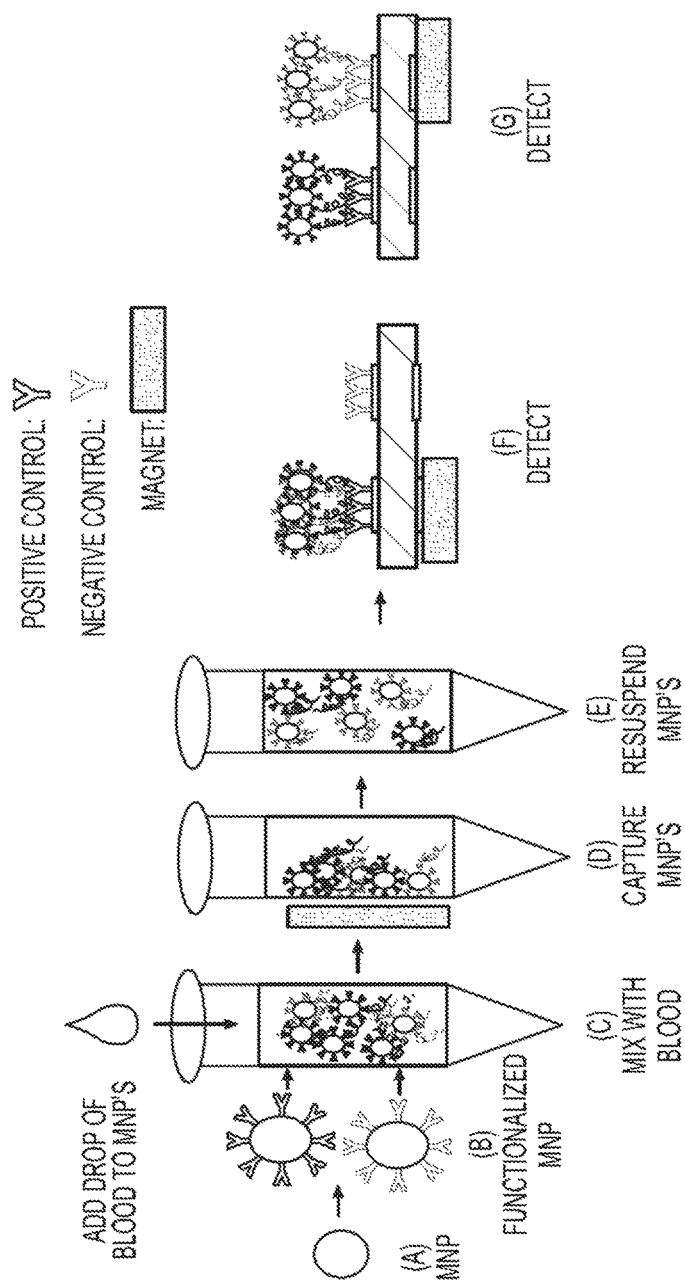
FIG. 30 is a schematic demonstrating Magnetic Nanoparticle (MNP) based sample processing and VHF biochip signal amplification.
Figure 31:
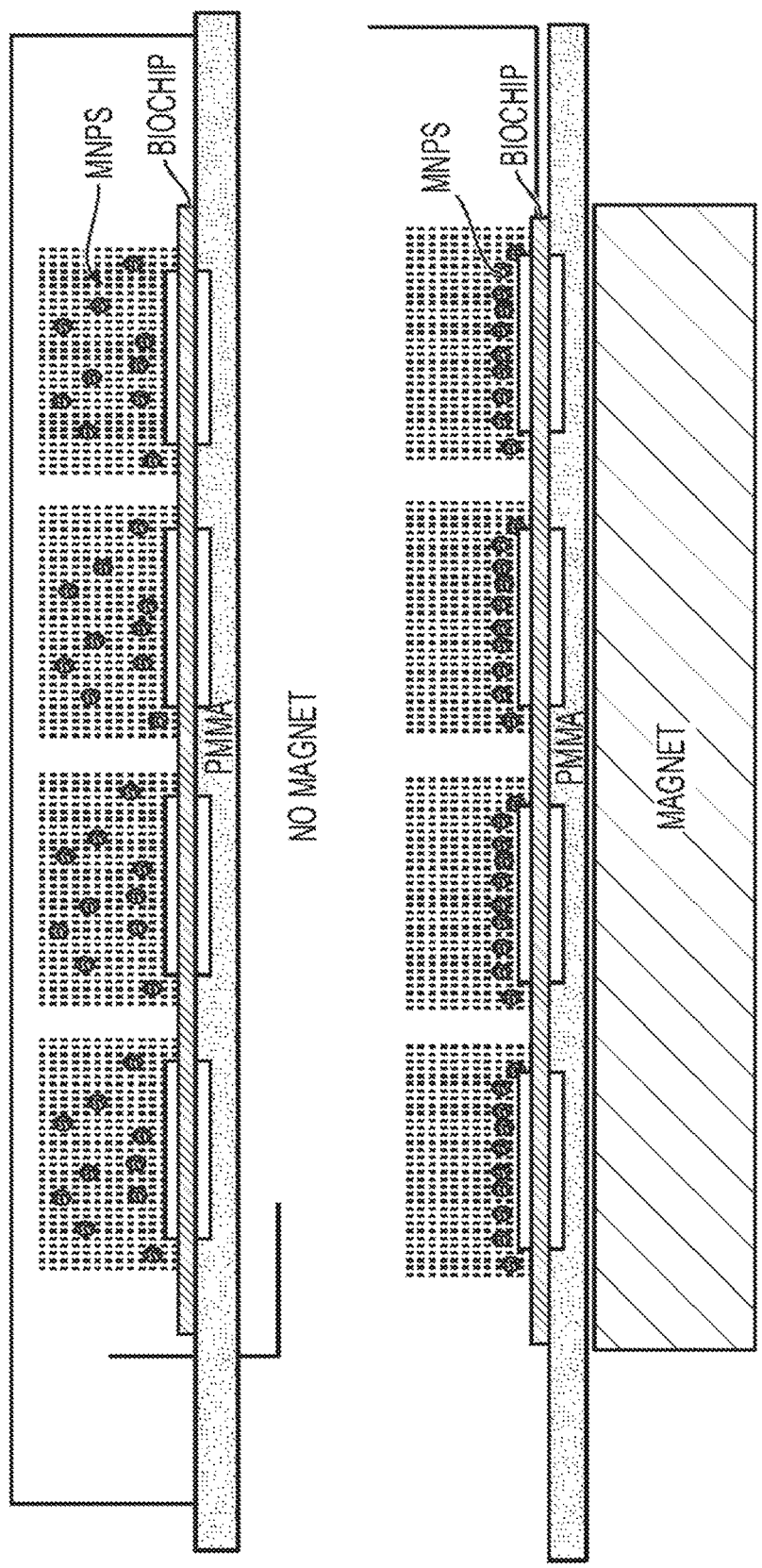
FIG. 31 is a schematic diagram showing rapid trapping of MNPs at the VHF biochip sensors.
Figure 32:
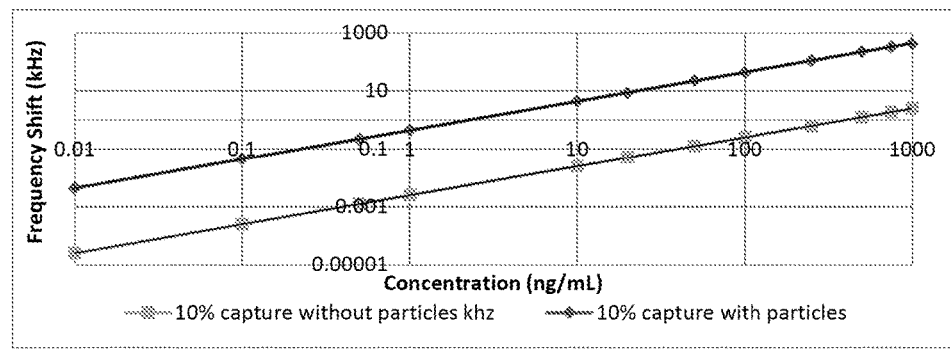
FIG. 32 is a theoretical plot demonstrating the potential improvement in detection signal (frequency shift) using MNP's as compared to experiments not using MNP's.
Figure 33:
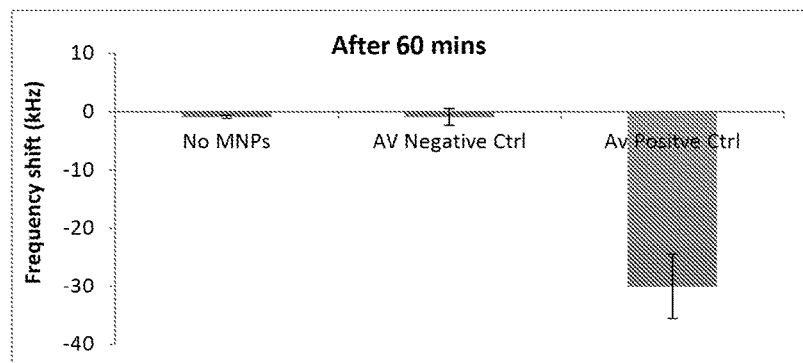
FIG. 33 shows detection of AFP with MNP's after a 60-minute on-chip incubation time.
Figure 34:
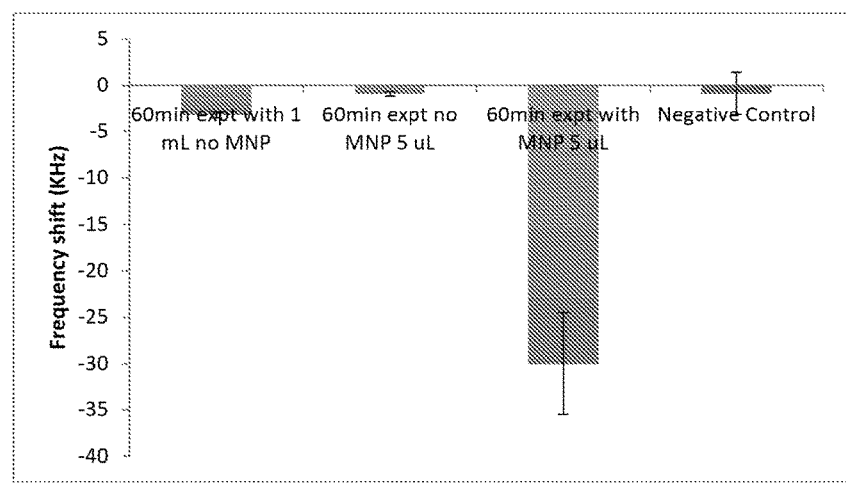
FIG. 34 shows a comparison of 60-minute experiments with and without MNP's.
Figure 35:
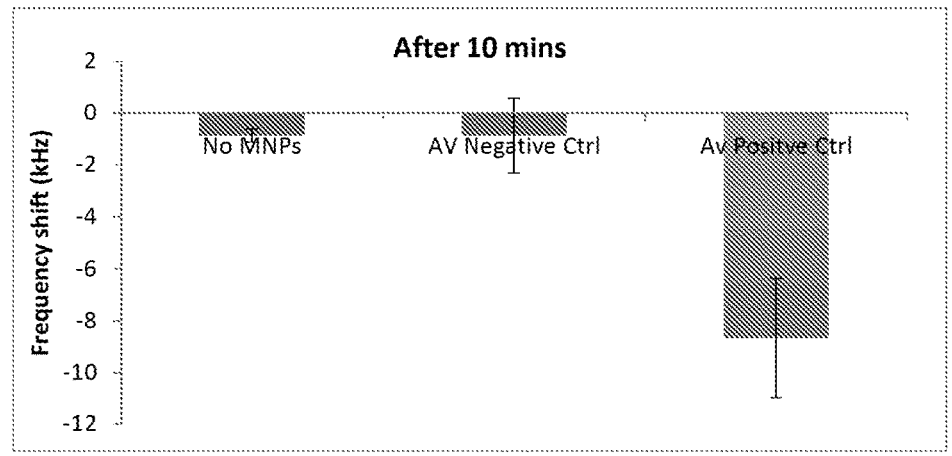
FIG. 35 shows the detection of AFP with MNP's after a 10-minute on-chip incubation time.

The experimental testing of biochips 102 is shown in FIGS. 30-32.

EXAMPLES

Example 1—Experimental Testing of the VHF Biochip for the Detection of AFP

Figure 28:
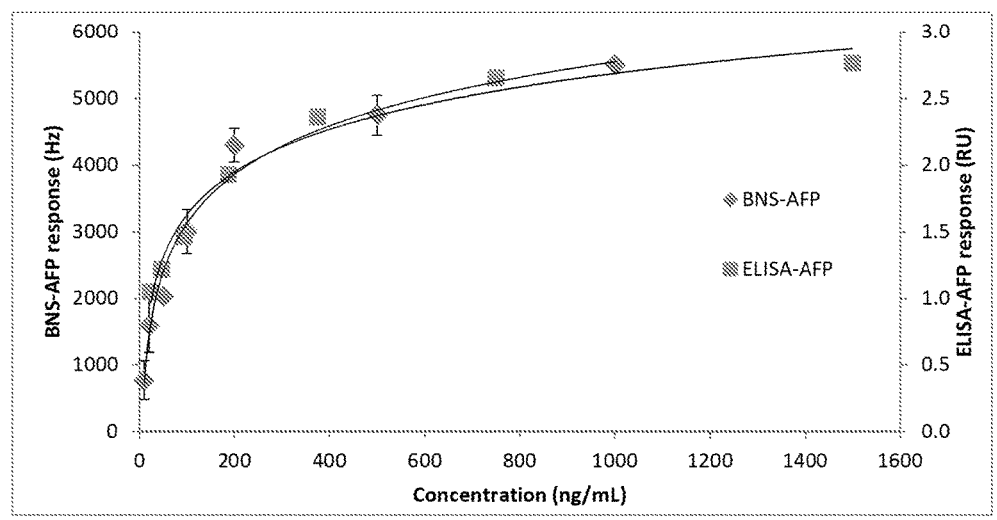
FIG. 28 is a graph of the standard curve for the detection of AFP on the VHF biochip demonstrating results comparable to the industry recognized ELISA-AFP test.

Biochip 102 was successfully tested for the detection of AFP concentrations ranging from 10-1500 ng/mL. Furthermore, 100 ng/mL AFP, in 20 uL of serum was successfully detected in approximately 20 minutes. Although clinically, if a patient has above 100 ng/mL of AFP it is a good indicator of liver cancer, it is necessary to detect much lower concentrations to differentiate healthy patients from sick patients. Therefore, a standard curve for AFP detection in serum is generated for AFP concentrations ranging from 20-1500 ng/mL. The next step was to test the system for detection of 10-1500 ng/mL AFP in serum and compare the results to ELISA test results as shown in FIG. 28.

These experiments were performed on standard distributed laboratory systems.

Experimental Setup:

This laboratory bench-top included an enclosure 104 encapsulating the AFP specific biochip 102. The measurement electronics consisted of a network analyzer 110, an RF switch 108, and a computer 112 for recording and plotting the data. An external four channel pump 106 was used for delivering, flowing and circulating the sample through the enclosure 104. The pre-functionalized (with anti-AFP capture antibodies Genway 57) VHF biochips were enclosed in the PDMS structure which was then connected to the electronic measurement system used to excite the biosensors and to a peristaltic pump to flow sample over the biochip 102. First, a blocker was flowed through system to block the tubes and non-functionalized regions of the VHF biochip to prevent non-specific binding. Next, the unbound blocker was washed away and a baseline with buffer was recorded (PBS-T-1 in FIG. 27A). The sample was allowed to incubate following which it was washed with buffer and the second baseline PBS-T-2 was recorded. Since the secondary antibody was in phosphate buffered saline (PBS), a third baseline, PBS-1 was recorded following which the secondary antibody Genway 99 was flowed through the system.

Figure 27A:
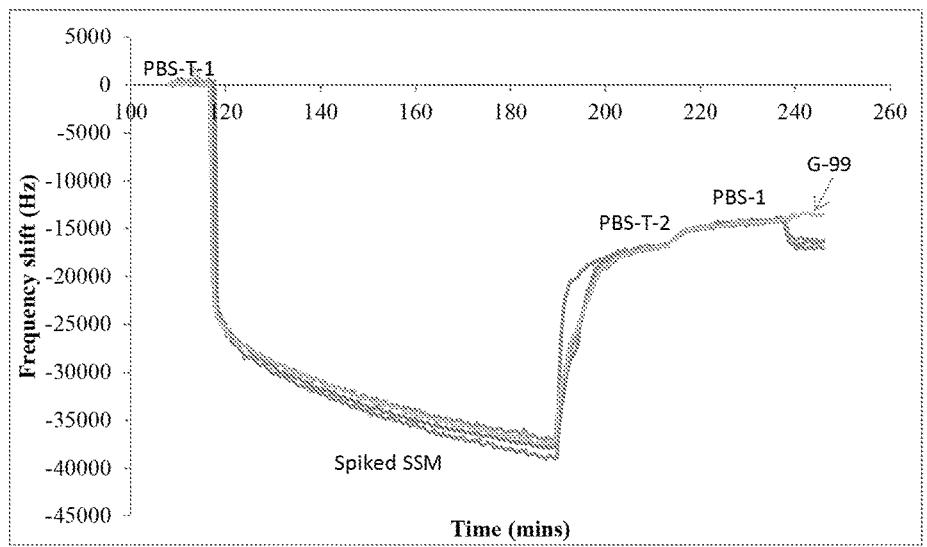
FIG. 27A is a graph of the real time frequency shift over time for the detection of 100 ng/mL Alpha Fetoprotein (AFP), the Liver Cancer biomarker, in human serum on the 4-sensor VHF biochip.
Figure 27B:
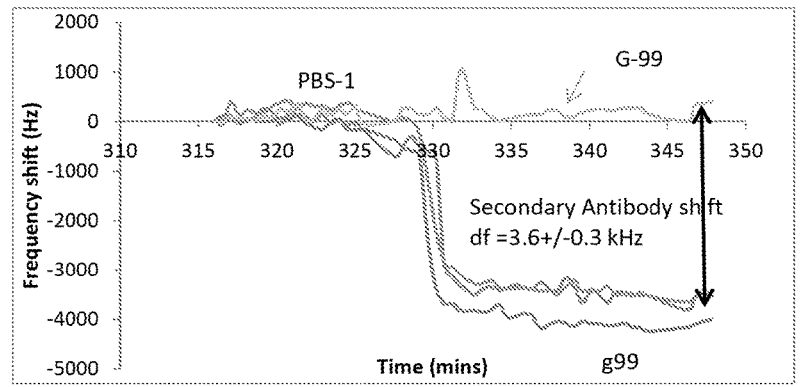
FIG. 27B is a zoomed-in view of the final detection step of FIG. 27A, demonstrating the difference between the positive controls and the negative control.

Of the 4 VHF sensors, three had the primary/capture antibody (Genway 57) and one had no antibody. As can be seen from the last loading step, three sensors immediately responded to the loading with Genway 99 whereas one sensor, the negative control, did not respond. Subtracting the negative control frequency shift from the average of the remaining three positive controls gives the detection signal which is a function of the concentration of AFP in the sample. This entire process can be recorded in real time, an example of which is shown in FIG. 27A. FIG. 27B is an expanded version of the last experimental step wherein the Genway 99 antibody is added.

Several factors play a role in the successful detection of AFP, including a low noise biochip 102, an optimized biochip 102 cleaning protocol, a highly sensitive primary and secondary antibody, an effective blocking agent, optimized concentrations of antibodies, optimized immobilization and blocking times and optimized washing steps.

Using the sandwich-assay detection protocol, the experiment was repeated for concentrations ranging from 10-1000 ng/mL in triplicate. The results of these experiments are shown in the figures. As can be seen, biochip 102 successfully detected AFP over concentrations ranging from 10-1000 ng/mL in a reproducible manner Next, this result was compared to an identical experiment conducted using a standard ELISA system.

Comparison of VHF-AFP and ELISA-AFP Detection.

The results of these tests were plotted on the same graph to compare the two methods as shown in FIG. 28. The results of the VHF biochip system 100 correlate well with the ELISA-AFP system. VHF biochip system 100 utilized a similar sandwich assay as that used in the ELISA-AFP system except for the shorter detection time because no development of the optical tag was required in the VHF biochip system 100.

The above experiments were performed using a large volume (1 mL) of spiked serum and the sample was run for a period of 1 hour. This was done to ensure similar incubation times as for the ELISA system, thus allowing for comparison of the results. The above results demonstrate that VHF biochip system 100 has a sensitivity similar to that of the ELISA system using the current protocols.

The next step was to demonstrate that VHF biochip system 100 is capable of detecting AFP in a short period (20 minutes).

Example 2—Reduced Time (20 Minutes)

A 20-minute test is more relevant for point-of-care testing. A protocol was developed to demonstrate detection of 100 ng/mL AFP in human serum wherein the sample is flowed over the VHF biochip for a period of 10 minutes, followed by a 7-8-minute washing step and a 2-3-minute secondary antibody step.

Figure 29A:
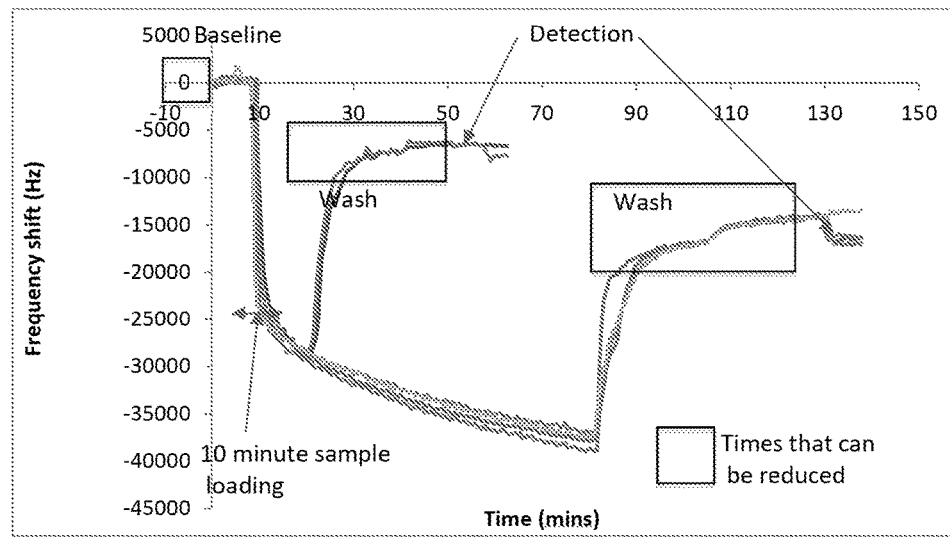
FIG. 29A is a graph of the real time detection of a 100 ng/mL concentration of AFP using a short (10-minute) and long (60-minute) incubation time.
Figure 29B:
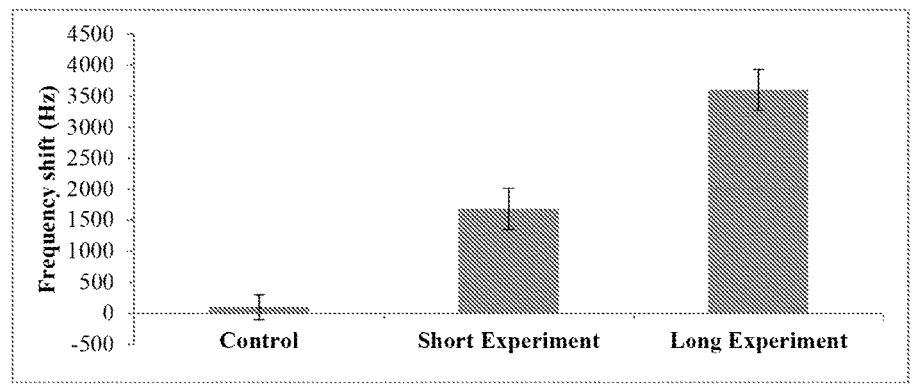
FIG. 29B is a bar column graph comparing experimental results of a long (60-minute) and short (10-minute) detection time for a concentration of 100 ng/mL AFP in serum.

The results of a standard long experiment and the 20-minute experiment are shown in FIGS. 29A and 29B. The result shown in FIG. 29A demonstrates successful detection of AFP in under 30 minutes. Next the biosensor 114 was washed. In future embodiments, the dead volume will be greatly reduced when the enclosure and fluidics are miniaturized thereby reducing the areas in grey shown in FIG. 29A will be reduced to 2-5 minutes.

Next, the secondary antibody is loaded and compared to a control sensor. AFP was successfully detected when biosensor 114 was loaded with the secondary antibody.

As can be seen in FIG. 29B, a standard 1 hour experiment gives a detection signal of 3.6±0.3 kHz whereas a 20-minute experiment gives a detection signal of 1.6±0.3 kHz. This signal is clearly differentiable from the control experiment. This decrease in signal is expected as the sensor is exposed to fewer antigens, however it is still capable of successfully detecting concentrations of 100 ng/mL in under 20 minutes.

Several modifications can be carried out to improve biosensor response in a short period of time. The current response corresponds to only a 1% capture efficiency of the antigen which can be improved by improving the biological interface or using a biochip 102 vibrating at a higher frequency.

In terms of biochip 102 and enclosure 104, operating at two times the frequency increases the mass sensitivity by four times. A miniature enclosure enables more efficient sample delivery to the sensors to improve capture efficiency. Also, the measurement electronics can be improved to provide an improved signal-to-noise ratio and therefore allow detection of lower concentrations in the sample.

In terms of the biological interface, several modifications can be made. For example, self-assembled monolayers would permit better orientation of antibodies and therefore improved antigen capture efficiency. A more sensitive antibody will also improve the capture efficiency. Nanoparticles can be used to amplify the mass loading effect and therefore reduce detection time and capture efficiency.

The biochip 102 successfully detected AFP in a concentration range from 10-100 ng/mL in human serum. The biochip 102 standard curve correlated to that of the standard ELISA results for AFP detection. Concentrations of 100 ng/mL in serum were detected in 20 minutes demonstrating that the biochip 102 can meet point-of-care requirements. The number of sensors that are required will depend on substrate size and resonant frequency. A 20 mm×20 mm 100 MHz chip could include 1-100 sensors.

A biological interface that is sensitive and selective to AFP and facilitates its rapid detection was developed. In the case of AFP detection system 400, biosensors 114 are made selective by functionalizing them with antibodies specific to AFP. In order to successfully do so the following tasks have to be completed. First, determine the appropriate antibody and antibody concentration to be used for detection. Second, determine the most effective blocking agent for the VHF biochip system 100. Third, determine the detection protocol for the VHF biochip system 100. Fourth, perform a 100 ng/mL AFP detection test in human serum.

In order to decrease the variability between the response of different sensors to serum loading a 75:25 mixture of human serum to sample was used. This mixture gave reproducible results at the serum level shown in FIG. 27A.

A mixture of salt, bovine serum albumin (BSA), dextran and Tween 20 with human serum was used to reduce non-specific binding. By increasing the salt concentration, the ionic strength of the mixture is increased thus lowering the electrostatic attraction of human serum proteins to the sensor, and thus a high concentration of salt was used. Dextran and BSA were added to reduce/prevent serum protein adsorption on the sensor surface, whereas detergents were used to stabilize the solution (reducing clustering) and thus reduce non-specific binding.

The variation between sensors when loaded with the serum mixture is greatly reduced upon washing. The difference between the PBS-T-1 and PBS-T-2 for each biosensor 114 was recorded for an average of 10 readings followed by calculation of the average and standard deviation of the averages for each sensor. The standard deviation was reduced from ±3.6 kHz to ±0.5 kHz.

In order to avoid the problem of false positive results, a secondary antibody may be used. Prior to performing detection experiments with AFP in the system 100, a sandwich assay was performed using ELISA, in serum, to determine the standard curve.

The standard curve for the detection of 20-1500 ng/mL AFP in serum using G57 antibody as the capture antibody and G99 antibody as the detection antibody is shown in FIG. 28. The system 100 was then tested for detection of a concentration of 100 ng/mL AFP using G57 antibody as the capture antibody and G99 as the detection antibody.

The 4 biosensors 114 were coated with G57 capture antibody. The channels and non-functionalized area of VHF biosensors 114 were then blocked with 3% BSA. Biosensors 114 were then washed with 0.1% Tween-20 in PBS. Next, biosensors 114 were loaded with serum mixture spiked with 100 ng/mL AFP while biosensor 114 was loaded with healthy serum mixture. Biosensors 114 were then washed with PBS-T-2 and PBS-1. Next all 4 sensors were loaded with G99 detection antibody. This can be seen in FIG. 27A

As shown in FIG. 27B, on loading the biosensors 114 with G99, within a couple of minutes a difference between the control biosensor 114 and the biosensors 114 that were loaded with AFP can be seen. This demonstrates the successful detection of 100 ng/mL of AFP in serum. The biosensors 114 that captured the AFP shift from the baseline PBS-1 level when loaded with G99 does not respond to G99 loading alone.

The VHF biochip response to 100 ng/mL AFP was 3.6+/−0.3 kHz. To summarize: This secondary antibody method enables rapid differentiation of AFP from other serum proteins. 1-2 minutes of loading with secondary antibody is all that was needed. More importantly, this method effectively eliminates false positive results as the secondary antibody is highly specific to the antigen of interest.

A number of AFP capture and detection antibodies were studied on the ELISA system and it was found that primary/capture and secondary/detection antibodies were the most sensitive capture and detection antibodies, respectively. An extensive study on the washing and blocking of the biochip 102 to prevent non-specific binding was conducted on both biochip 102 and ELISA system. It was found that using 75% human serum with 25% of mixture leads to a minimum amount of non-specific binding and variability between sensors.

The sizes of the electrodes 120 and wells 132 were optimized for an improved signal-to-noise ratio and stability. Preferably, a diameter of the electrode 120 is about 0.762 mm and the diameter of the well 132 is about 1 mm. In this particular embodiment, these dimensions were determined to be optimal. However, it should be understood that the diameter of the electrode 120 may be between 0.01 mm to 1.5 mm, more preferably between 025 mm and 0.90 mm, and most preferably between 0.4 mm and 0.8 mm. The diameter of well 132 may be between 0.01 mm to 1.5 mm, more preferably between 0.25 mm and 1.25 mm, and, most preferably, between 0.6 mm and 1.1 mm.

An enclosure 504 was also designed and constructed to demonstrate an improvement in the quality factor from 1000 to almost 2000, thus enabling an improved signal-to-noise ratio.

It was determined that Genway 57 gave the maximum response to AFP loading and thus was therefore selected as the primary/capture antibody. On the other hand, Genway 99 gave a lower response to AFP loading but the rate of detection at higher concentrations was higher than that of Genway 57. Therefore, Genway 99 was selected as the secondary/detection antibody.

Utilizing these primary and secondary antibodies to form a sandwich assay, AFP was detected on the ELISA system for concentrations ranging from 20-1500 ng/mL. Next, the protocol as translated and modified for the VHF biochip. The VHF biochip successfully detected AFP in human serum at concentrations ranging from 10-1000 ng/mL. Comparison of ELISA and biochip 102 results for the detection of AFP in human serum demonstrated that the VHF biochip's performance correlates well with that of ELISA.

In order to demonstrate that biochip 102 is capable of detecting AFP in a short period of time, a 20-minute experiment was successfully conducted for the detection of 100 ng/mL AFP in human serum.

Figures 36A, 36B:
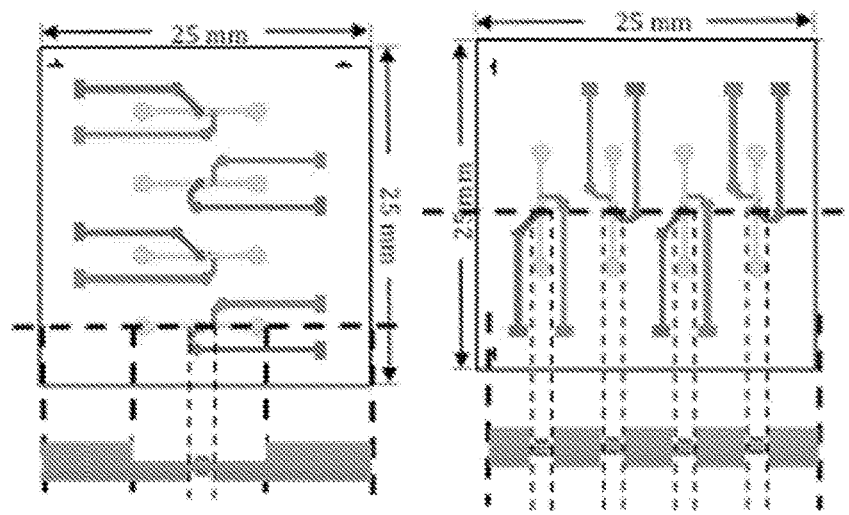
FIG. 36A is a top view of a horizontal plane cross-section of the 4-sensor VHF biochip design taken through a microfluidic channel.
FIG. 36B is a top view of a horizontal plane cross-section of the 4-sensor VHF biochip design with a taken through the center of the substrate.
Figure 37:
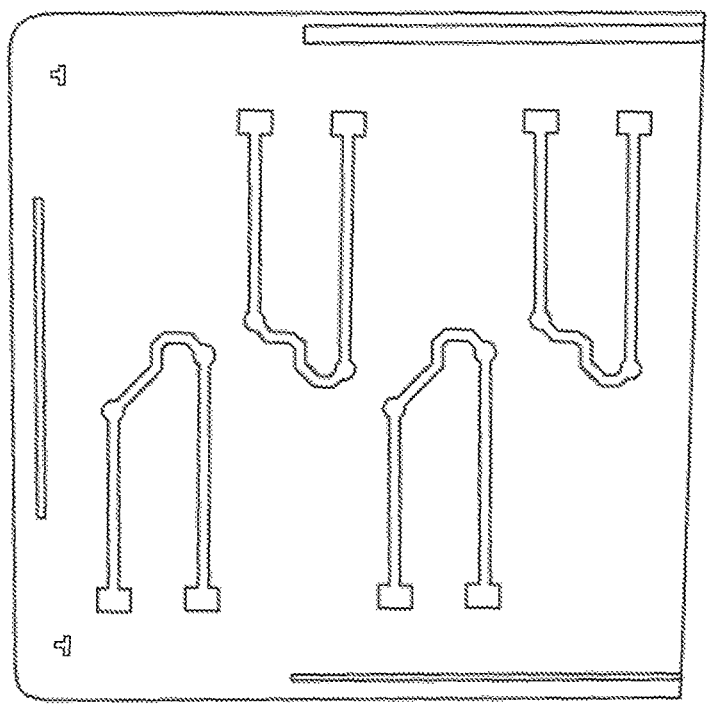
FIG. 37 is an image of the fabricated 4-sensor VHF biochip with uncoupled fluidic channels.
Figure 38:
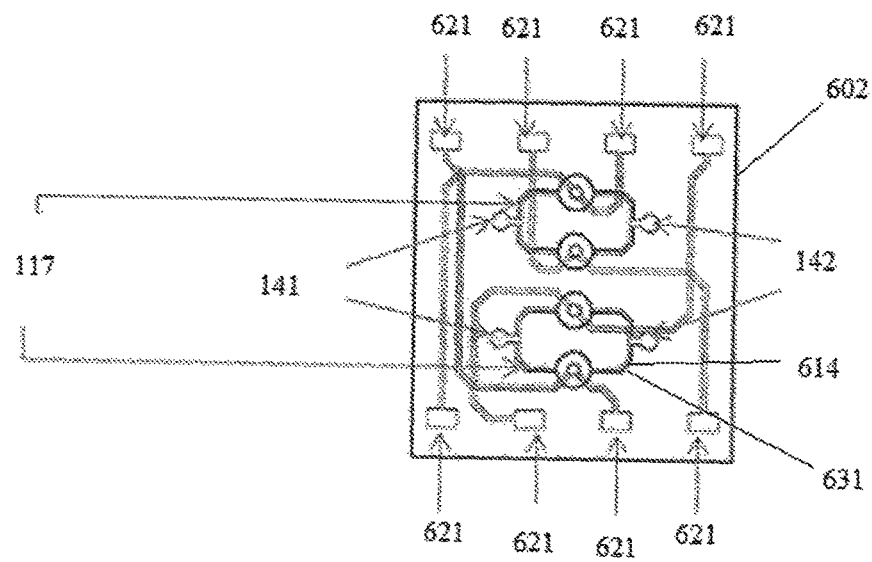
FIG. 38 is the design of a 4 sensor biochip with coupled microfluidic channels.
Figure 39:
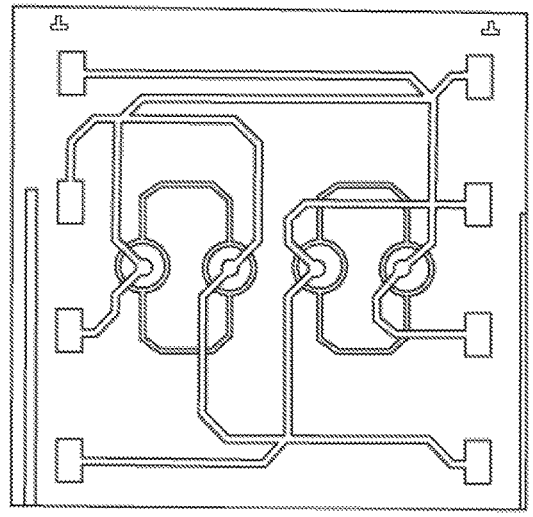
FIG. 39 is an image of the fabricated 4 sensor VHF biochip with coupled microfluidic channels.

Several VHF biochip configurations with different electrode 120, electrical trace 130 and fluidic channel 117 orientations have been designed as shown in FIGS. 37-45. FIG. 39 represents a biochip 102 design similar to FIG. 16 with a difference in its electrical traces 130 and tabs 121. This design has 4 un-coupled fluidic channels 117, each with its own inlet 141 and outlet 142. FIG. 36A is the top view of the 4-sensor VHF biochip 102 design in cross-section taken along a microfluidic channel 117. In this design there is one biosensor 114 along each channel. The fluidic channel 117 is etched into the top of the biochip substrate 118. A well 132 is etched into the bottom of the substrate 118. The electrodes 120 for exciting the biosensor 114 are deposited to sandwich the quartz between the channel 117 on the top and the well 132 on the bottom. The traces 130 are brought out of the channel 117 on the top and the well 132 on the bottom of the substrate 118.

FIG. 36B is the top view of the 4-sensor VHF biochip 102 design with a cross-section taken through the center of the substrate perpendicular to the channel 117. There are four sensors 114, one per channel 117 on the top of the biochip 102, aligned with the wells 132 on the bottom of the substrate.

The designs shown in FIGS. 36A-B were then fabricated by the process described previously resulting in a 4-sensor VHF biochip 102 as seen in FIG. 37 with uncoupled fluidic channels A biochip 602 with a modified configuration of fluidic channels 117 and electrical traces 130 is shown in FIG. 38. Here two fluidic channels 117 are coupled with a single inlet 141 and outlet 142 and one biosensor 114 along each of the two channels 117. The fluidic channels 117 are only present on the top surface of the substrate 118 or biochip 102. Wells are etched into the bottom of the substrate 118. The electrical trace configurations are shown in FIG. 38 terminating in electrical tabs 621 that interface with an excitation source. This configuration can be used for testing the positive control in duplicate (along one of the coupled channels) and the negative control in duplicate along the second coupled channel FIG. 39 is an image of the fabricated 4 sensor VHF biochip 102 with coupled microfluidic channels 117

Figures 40A, 40B:
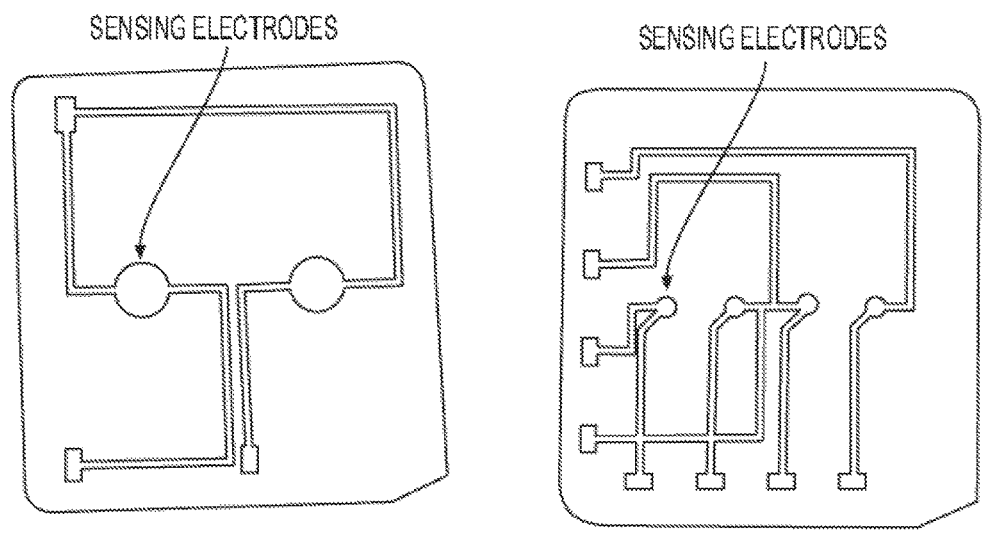
FIG. 40A an image of a fabricated 2 sensor VHF biochip.
FIG. 40B is an image of a fabricated 4 sensor VHF biochip with electrical traces on perpendicular edges.
Figure 41:
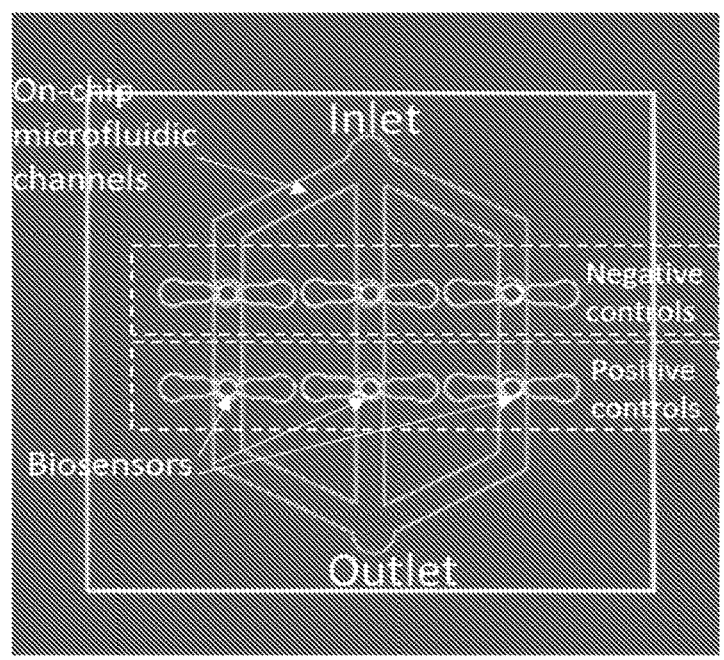
FIG. 41 is a VHF biochip design with multiple sensors per channel and coupled channels.

Two other embodiments of the biochip 102 are shown in FIGS. 40A and 40B. FIG. 40A is an image of a fabricated 2 sensor 22 MHz VHF biochip. FIG. 40B is an image of a fabricated 4 sensor 100 MHz VHF biochip 102 with electrical traces 130 on perpendicular edges. FIG. 41 is another potential embodiment of the VHF biochip 102 design with multiple sensors 114 per channel 117 and coupled channels 117. Here there is only one inlet 141 and one outlet 142. Sample coming in is split along three channels 117 and tested in triplicate. There are two sensors 114 per channel 117 for a positive and a negative control along each channel 117. This embodiment is useful for the detection of a single biomarker in triplicate. To detect multiple biomarkers the number of sensors 114 along each channel 117 can be increased.

Figure 42:
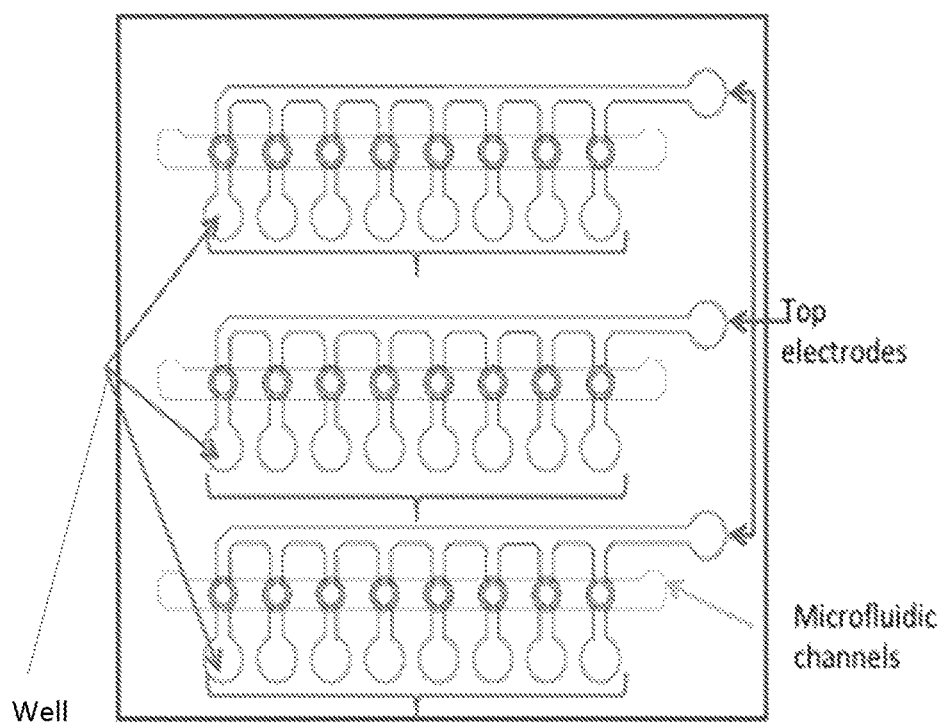
FIG. 42 is a VHF biochip design consisting of three parallel individual channels with 8 sensors along each channel.

FIG. 42 is a VHF biochip 102 design consisting of three parallel individual channels 117 with 1 to 8 or more sensors 114 along each channel 117. Electrical connectivity consists of the shorting of all the top sensing electrodes 120, once they are brought out of the fluidic channel 117 resulting in a requirement for a single electrical connection. The bottom electrodes 120 are un-coupled.

The Top electrodes 120 and the microfluidic channel 117 are on the same side of the substrate.

The number of sensor 114 per channel 117 can be increased/decreased based on the number of analytes to be detected. The number of channels 117 can also be increased/decreased based on the number of repetitions of the tests that are required (e.g. for triplicates there would be 3 channels).

Each channel 117 has an even number of sensing elements 114 wherein half will be dedicated as controls and the remainder dedicated to detection of analytes. Every sensing element 114 along a channel 117 detects a different analyte. Duplicates/triplicates will be detected along parallel channels 117. This VHF biochip 102 design allows for overcoming currently encountered complex and limiting features (in terms of size, speed, number of sensors and fluidic sealing), thus enabling high throughput multi analyte detection.

All current state of the art piezoelectric sensor technologies consist of sensors 114 with individual pairs of top and bottom electrodes 120, a format that limited the size and number of sensing elements. This is because each sensing element 114 has its own dedicated pair of electrodes and dedicated electrical trace. Thus for a size limited structure, increasing the number of elements is constrained by the number and complex design of the traces 130. This also leads to difficulty in fluid channel 117 sealing.

The new method shorts the electrical traces 130 on the side of the wafer 118 where the fluidic channels 117 are etched. Therefore, instead of multiple traces 130 there is just one trace 130 to be connected to the external source. The bottom surface is isolated from the fluidic channel and will be connected to the excitation source via electrical contacts printed on a contacting layer. Activation would involve simply switching between bottom electrodes 120 while holding the top shorted electrode at ground.

The trace lengths for each sensing element 114 will be maintained constant. New VHF sensor designs that reduce complexity and allows for excitation of multiple sensor 114 with reduced number of traces 130. Due to the reduced number of traces 130 this design allows for better electrical isolation from fluidics and improved fluid channel 117 sealing. The new design also allows for the increase in the number of sensing elements 114 per channel 117 thus facilitating the detection of a number of analytes in the same sample. Due to reduced trace numbers, the design of the electromechanical encapsulating structure that encloses biochip 102 is simplified. The design calls for shorting and grounding of a top electrode 120 that comes in contact with a fluid to reduce electrical influence on detection.

Figure 43:
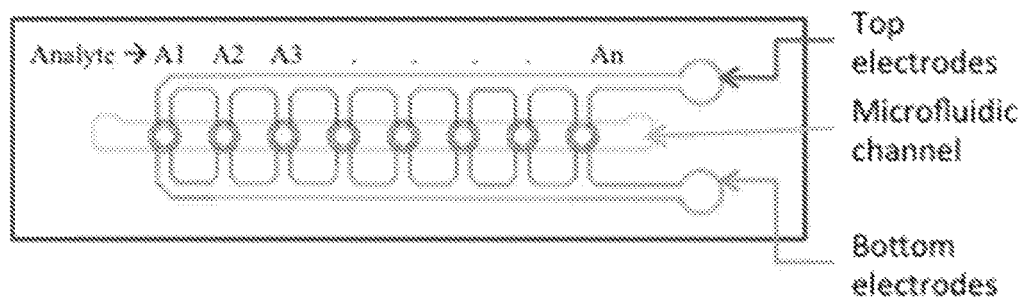
FIG. 43 is a VHF biochip design with a single channel having 8 sensors for the simultaneous detection of 1-8 antigens/biomolecules.

FIG. 43 is a VHF biochip 102 design with a single channel 117 having 1-8 or more sensors 114 for the simultaneous detection of 1-8 or more antigens/biomolecules. All the top electrodes 120 are shorted resulting in a single connection. The same is done for the bottom sensors 114. The frequency of each sensor 114 can be differentiated by either etching each to a different depth or by introducing electrical components in the excitation path thus separating the peaks. The top electrodes 120 and the microfluidic channel 117 are on the same side of the wafer.

The number of sensors 114 per channel 117 can be increased/decreased based on the number of analytes to be detected. The number of channels 117 can also be increased/decreased based on the number of repetitions of the tests/analytes that are required (e.g. For triplicates there would be 3 channels). Each channel 117 has an even number of sensing elements 114 wherein half will be dedicated as controls and the remainder dedicated to detection of analytes. Every sensing element 114 along a channel 117 detects different analytes.

Duplicates/triplicates will be detected along parallel channels 117. This biochip design allows for overcoming currently encountered complex and limiting features (in terms of size, speed, number of sensors and fluidic sealing), thus enabling high throughput multi analyte detection.

The new method shorts the electrical traces 130 on the side of the wafer 118 where the fluidic channels 117 are etched. Therefore instead of multiple traces 130 there is just one trace 130 to be connected to the external source. The bottom surface of the substrate 118 is isolated from the fluidic channel 117 and will be connected to the excitation source via electrical contacts printed on a contacting layer. Activation would involve simply switching between bottom electrodes 120 while holding the top shorted electrode 120 at ground.

The biochip design reduces complexity and allows for excitation of multiple sensors 114 with a reduced number of traces 130. Due to the reduced number of traces 130 the design allows for better electrical isolation from fluidics and improved fluid channel 117 sealing. The design further allows for an increase in the number of sensing elements 114 per channel 117 thus facilitating the detection of a number of analytes in the same sample. Due to reduced trace numbers, the electromechanical encapsulating structure that encloses the biochip 102 has a greatly simplified design.

Figure 44:
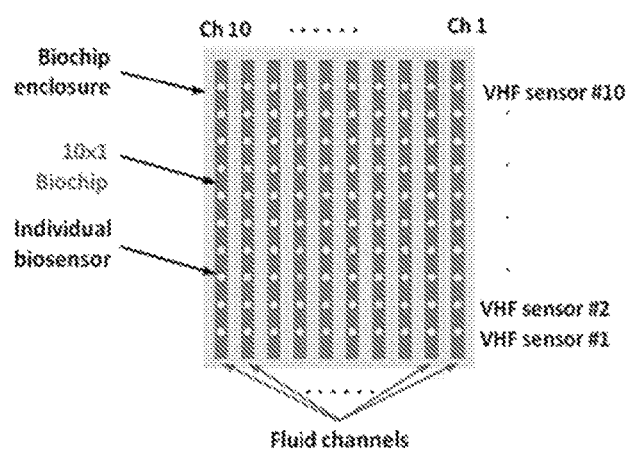
FIG. 44 is a schematic of a 10×10 VHF biochip 10 uncoupled or coupled channels having 10 along each channel, which can then be stacked to form a stack of biochips.

FIG. 44 is a schematic of a 10×10 VHF biochip 102 with 1-10 or more uncoupled channels which could alternatively be coupled, and having 1-10 or more sensors 114 along each channel. These can then be stacked to form a stack of 2-10 or more biochips 102 for high throughput applications.

Figure 45:
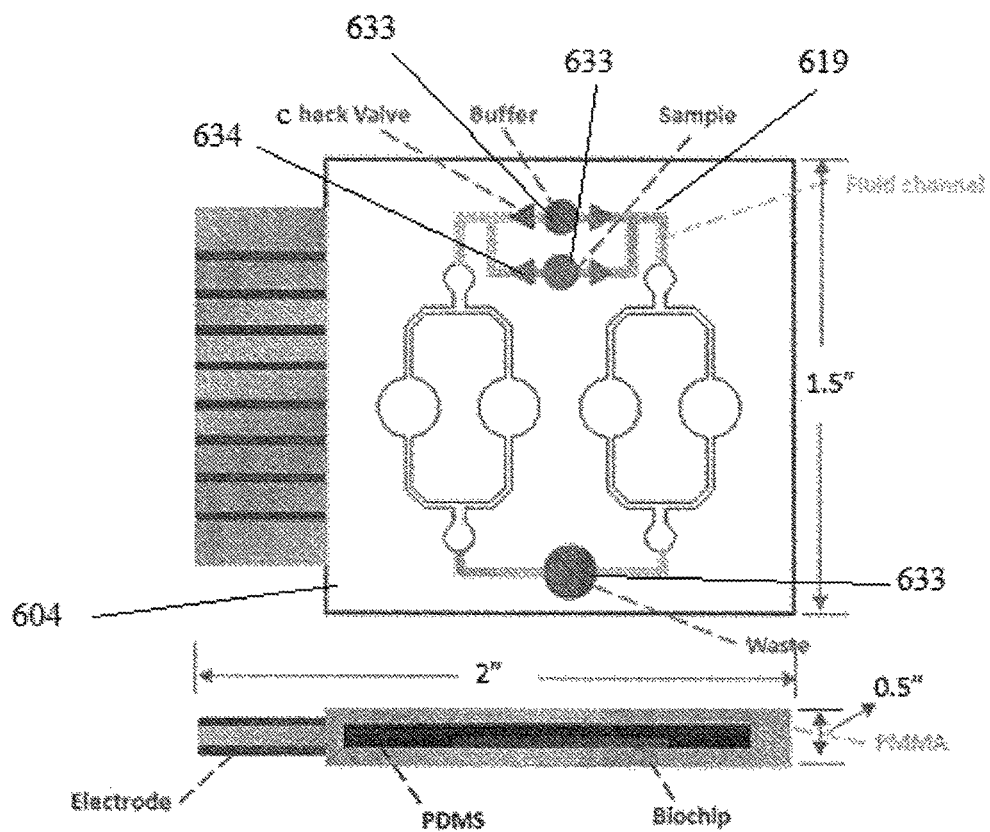
FIG. 45 is the top view of the VHF biochip enclosure.

Design of the enclosure 604 is shown in FIG. 45. In order to test biochip 602, it was placed in an enclosure 604 having the following features: three reservoirs 633 for waste, buffer, and sample solution, respectively. Fluidic enclosure channels 619 connect the reservoirs 633 to the biochip 602. Unidirectional flow from the reservoirs 633 to the chip 602 is ensured by one way check valves 634.

The enclosure 604 may comprise a polymer sealing layer around biochip 602 which is then surrounded by a hard shell. Electrical connections are used to connect the biochip 602 to the electrical tabs 621. This allows for ease of use of enclosure 604.

Figure 46:
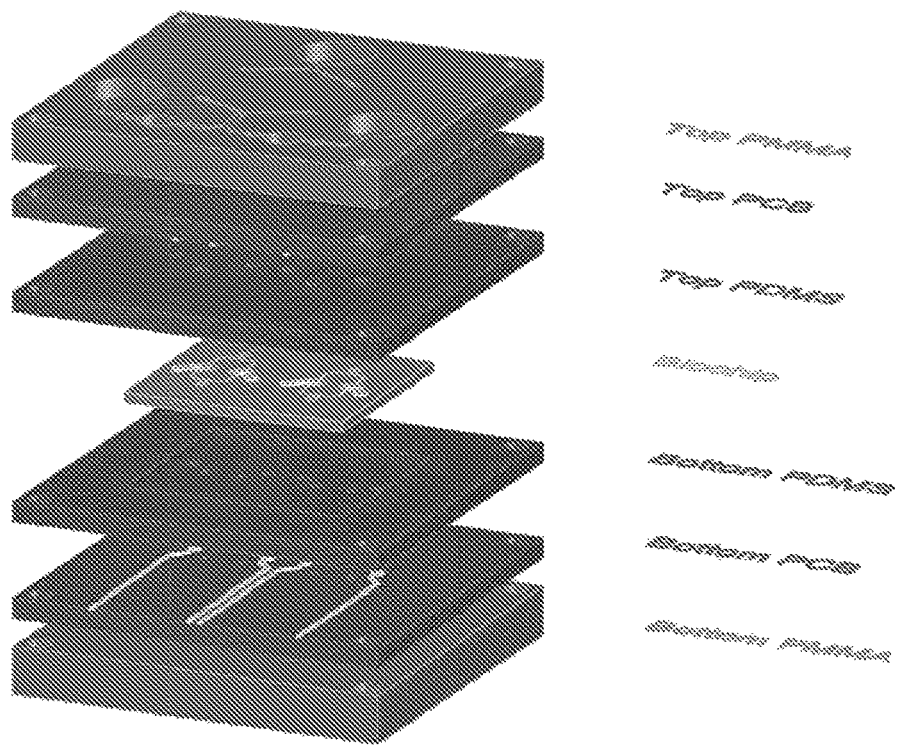
FIG. 46 is a schematic showing all the VHF biochip enclosure layers.

Referring to FIG. 46, the design shown therein consists of top and bottom layers 651, 653 of a hard protective material, possibly PMMA. The next layers 652, 654 are designed to enable the electrical excitation of the biochip 602. These are PCB layers with electrical tabs 621 aligned with electrical tabs 621 on biochip 602. The connection will be made via pogo pins (not shown), making contact with the biochip 602.

The enclosure 604 facilitates improved sensitivity by preventing loss of sample along fluidic channels 617. This allows for reproducible testing of biochips 602. This further allows for improved electrical connectivity via the use of pogo pins and a reduction in trace length thereby improving the Q-factor and sensitivity. This also overcomes the drawback of utilizing fragile high frequency biochips 602, by providing a rugged, protective, mechanical support.

Figure 47A:
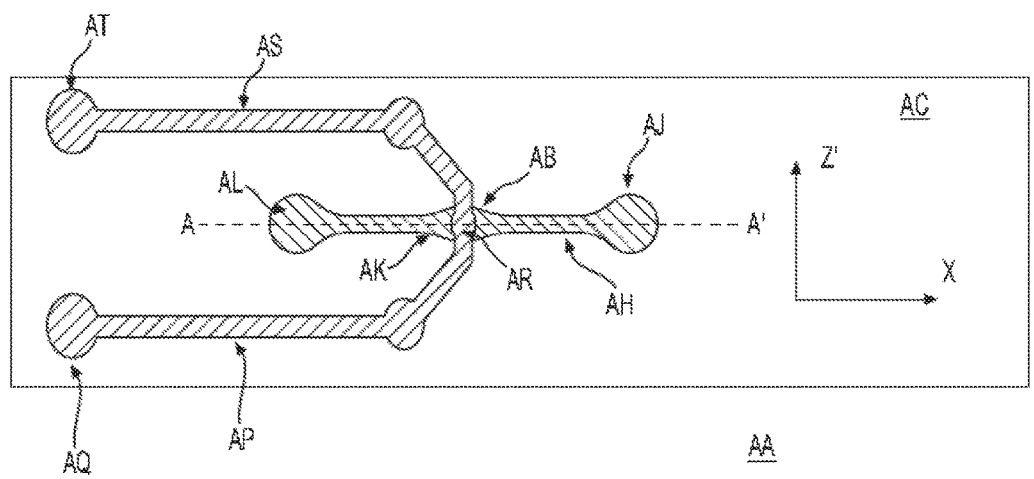
FIGS. 47A and 47C are top views of a biochip having a single biosensor.
Figure 47B:
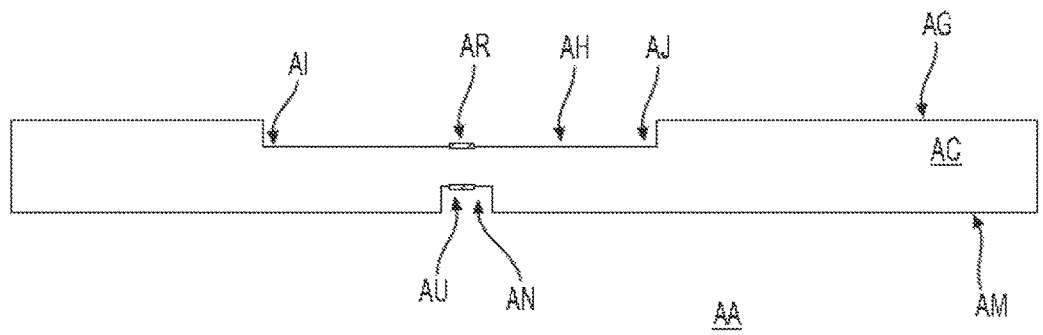
FIG. 47B is a cross-section side view of the biochip of FIG. 47A.
Figure 47C:
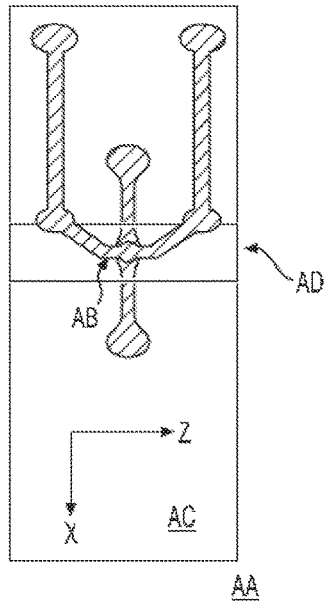
Figure 47D:
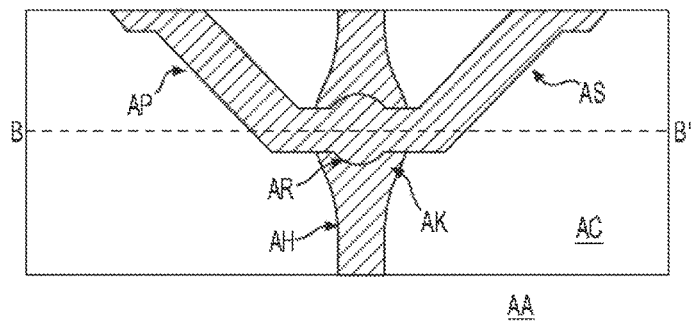
FIG. 47D is a magnified, top view of the biochip shown in FIG. 47C.
Figure 47E:
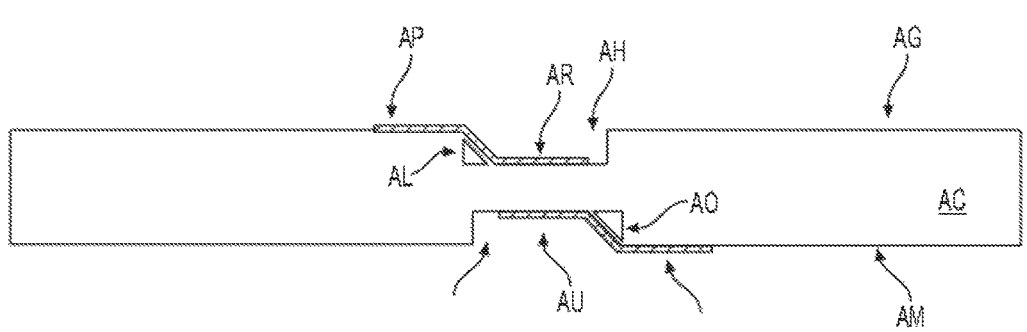
FIG. 47E is a cross-section side view of the biochip of FIG. 47D.
Figure 47F:
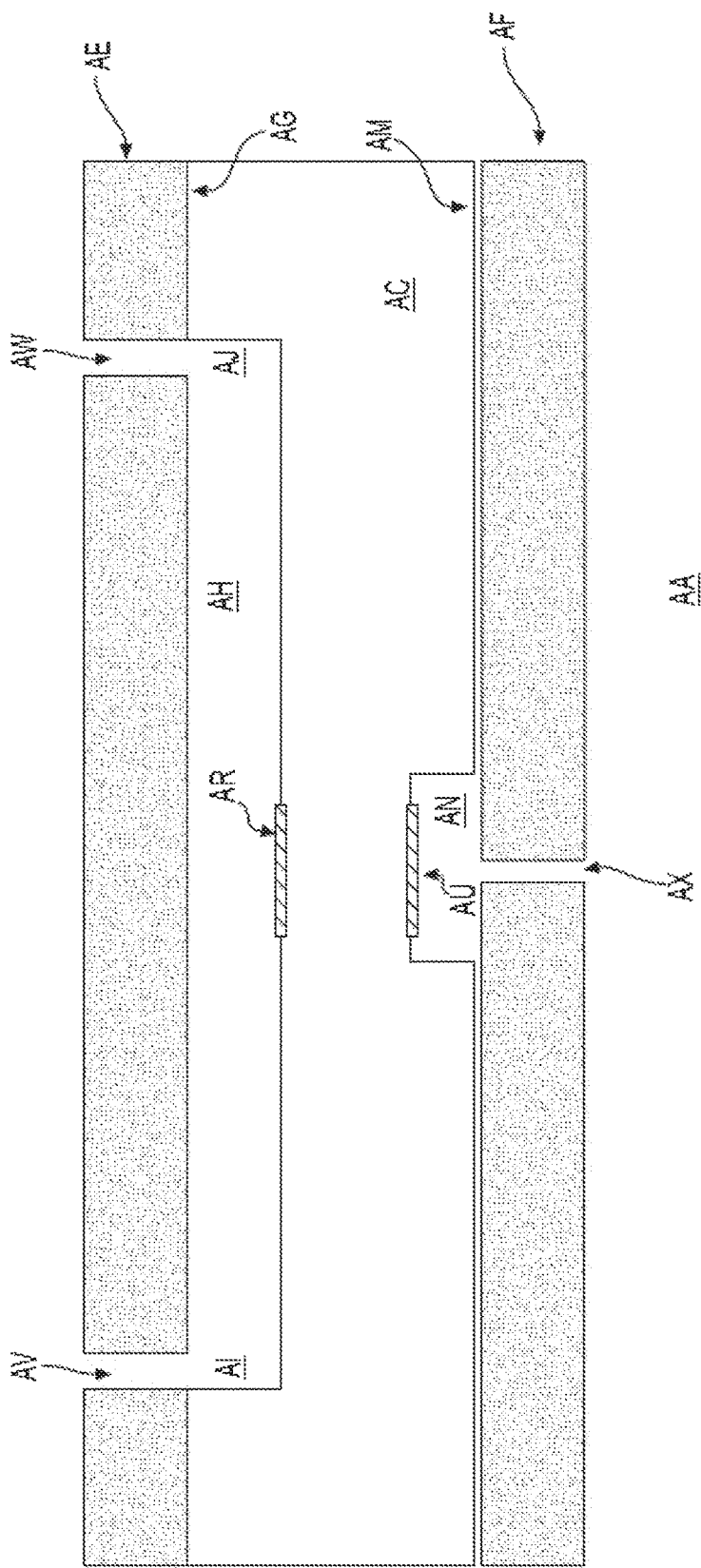
FIG. 47F is a cross-section side view of the biochip of FIG. 47A, where the biochip has top and bottom seal layers.

FIGS. 47A and 47C are top views of a biochip AA having a single biosensor AB formed on a piezoelectric (e.g., quartz) substrate AC. FIG. 47B is a cross-section side view of the biochip AA along the cut-line A-A' of FIG. 47A. FIG. 47D is a magnified, top view of the region AD of the biochip AA shown in FIG. 47C. FIG. 47E is a cross-section side view of the biochip AA along the cut-line B-B' of FIG. 47D. FIG. 47F is a cross-section side view of the biochip AA along the cut-line A-A' of FIG. 47A, where the biochip AA has top and bottom seal layers AE and AF. Note that these figures are not drawn to scale and are primarily intended to represent the features of the biochip AA, not the relative dimensions of those features.

Formed in the top surface AG of the substrate AC is a fluidic (e.g., microfluidic) channel AH having an inlet AI and an outlet AJ. Note that the fluidic channel AH also has a widened region AK. As shown in FIG. 47E, the sidewall AL of the fluidic channel AH is sloped at an angle less than 90 degrees.

Formed in the bottom surface AM of the substrate AC is a well AN. As shown in FIG. 47E, the sidewall AO of the well AN is also sloped at an angle less than 90 degrees.

Formed on the top surface AG of the substrate AC is an electrical (e.g., metal) trace AP that traverses from a tap AQ to an electrode AR that is formed within the widened region AK of the fluidic channel AH. Note that, as shown in FIG. 47E, the trace AP runs along the sloped sidewall AL to ohmically connect to the electrode AR. Side wall AL, with an angle less than 90 degrees, enables the electrical trace AP to connect with the electrode AR via a suitable process such as evaporation or deposition.

Formed on the bottom surface AM of the substrate AC is another electrical trace AS that traverses from a tap AT to an electrode AU that is formed within the well AN. Note that, as shown in FIG. 47E, the trace AS runs along the sloped sidewall AO to ohmically connect to the electrode AU. Side wall AO, with an angle less than 90 degrees, enables the electrical trace AS to connect with the electrode AU via a suitable process such as evaporation or deposition.

As shown in FIG. 47F, the seal layer AE on the top surface AG of the biochip AA has openings AV and AW corresponding to the inlet AI and the outlet AJ, respectively, of the fluidic channel AH. Similarly, the seal layer AF on the bottom surface AM of the biochip AA has an opening AX corresponding to the well AN to release any air that could be trapped while assembling the seal layer AF. Although not shown in the figures, the seal layers AE and AF also have openings corresponding to the taps AQ and AT, which are displaced from the fluidic channel AH, allowing for isolation of the electrical connections from the fluidics.

The electrodes AR and AU and the intervening portion of the substrate AC form the biosensor AB.

In the embodiment of biochip AA shown in FIGS. 47A-47F, the taps AQ and AT are formed on opposite surfaces AG and AM of the substrate AC. In alternative embodiments, one of the traces AP and AS extends to and around an edge of the substrate AC such that both taps AQ and AT are located on the same surface of the surface. For example, the trace AP on the top surface AG may extend to and around an edge of the substrate AC onto the bottom surface AM such that both taps AQ and AT are located on the bottom surface AM.

In the embodiment of biochip AA shown in FIGS. 47A-47F, the bottom surface AM has the well AN. In alternative embodiments, the bottom surface AM has a bottom fluidic channel analogous to the top fluidic channel AH on the top surface AG. In that case, the well AN will be a widened portion of the bottom fluidic channel analogous to the widened portion AK of the top fluidic channel AH. Note that the bottom fluidic channel can be, but does not have to be oriented parallel to or orthogonal to the top fluidic channel AH. Note further that the widened portions of the fluidic channels, such as the widened portion AK of the top fluidic channel AH, are optional.

The embodiment of biochip AA shown in FIGS. 47A-47F has only one biosensor AB. In other embodiments, a biochip may have multiple biosensors configured in a one-dimensional or two-dimensional arrangement on a single substrate. In the example embodiments shown in FIGS. 41-43, multiple biosensors share a single top fluidic channel structure. In the embodiments shown in FIGS. 42 and 43, multiple biosensors share a single top electrical trace structure. In the embodiment shown in FIG. 43, multiple biosensors share a single bottom electrical trace structure, while the bottom electrical traces in the embodiment of FIG. 42 are not ohmically shorted together on the biochip (i.e., the electrical traces are said to be independent electrical traces).

Note that, in the embodiment of FIG. 43, the depths of the different bottom wells may be different for the different biosensors such that the thicknesses of the intervening substrate structure will be different for the different biosensors and therefore the resonant frequencies of those different biosensors will be different. In the embodiment of FIG. 42, the substrate thicknesses may be the same or different for the different biosensors that share a single fluidic channel and a single top electrical trace structure.

Note that multiple biochips, each having one or more biosensors, can be configured in a one-dimensional, two-dimensional, or three-dimensional arrangement.

The present invention enables VHF biochips providing high sensitivity detection, small sensor size, and narrow fluidic channels. The use of etched fluidic channels and wells to the depth of the biosensors provides individual sensors that can be mechanically isolated from each other on a single substrate. The biochips can be mechanically strong since only the channel/well regions are thinned and not the entire substrate. The fluidic channels enable liquid to be injected at a location displaced from the biosensors, thereby reducing or even eliminating injection noise from the biochip response. Microfluidic channels enable simplified cartridge design and low sample volumes.

The fluidic channels and wells may be fabricated using a wet etch process which provides low roughness surfaces and non-vertical (i.e., less than 90 degrees) sidewalls, depending on the (e.g., quartz) crystal orientation. This enables the electrical traces to extend into the channels and wells, ensuring that the electrical connections to off-chip electronics are isolated from the liquids on the biosensor electrodes.

As shown in FIGS. 30 and 31, the biosensors can be used with magnetic particles (e.g., magnetic nanoparticles or MNPs). In the particular example scenario of FIG. 30, different MNPs of step (a) are functionalized in step (b) with two different molecules/proteins/antibodies that are known to bind with two different antigens, respectively. In step (c), the functionalized MNPs are mixed with the sample (blood, serum, urine, saliva, etc.) having both antigens, possibly using a rotating magnetic field to achieve thorough mixing. In step (d), a magnetic field is applied (e.g., using a magnet) to capture the MNPs, some or all of which are not bound with the corresponding antigens. The unbound sample is then removed and, in step (e), the captured MNPs are re-suspended in a suitable liquid. In step (f), the liquid is applied to a biochip having two biosensors that share a single fluidic channel: a first biosensor having its top electrode previously functionalized with molecules/proteins/antibodies specific to the first antigen and a second biosensor having its top electrode previously functionalized with molecules/proteins/antibodies specific to the second antigen. In step (f), a magnetic field is applied to draw the MNPs towards the top electrode of the first biosensor such that those MNPs bound with the first antigen will bind to the first molecule/protein/antibody. In step (g), a magnetic field is applied to draw the MNPs that are not bound with the first antigen to the top electrode of the second biosensor, where those MNPs bound with the second antigen will bind with the second molecule/protein/antibody. Appropriate alternating electrical fields can then be applied to the various electrodes to detect the presence of MNPs bound with the first antigen using the first biosensor and the presence of MNPs bound with the second antigen using the second biosensor. The alternating electrical fields can also be applied during the whole process to monitor and characterize the entire binding process in real time.

Such use of MNPs enables rapid sample processing by enabling functionalized MNPs to pull antigens of interest from complex solutions like blood/urine/saliva under the influence of a magnetic field. Using MNPs also enables (i) reduction in false positive results since non-essential blood components are discarded prior to detection, (ii) rapid detection due to rapid pulling of MNPs onto the biosensors of a biochip using magnetic fields, (iii) detection signal amplification due to the added mass of MNPs and captured antigen, and (iv) detection of multiple antigens simultaneously with multiple biosensors on a single biochip.

Although the invention has been described using relative terms such as "down," "out," "top," "bottom," "over," "above," "under" and the like in the description and in the claims, such terms are used for descriptive purposes and not necessarily for describing permanent relative positions. It is understood that the terms so used are interchangeable under appropriate circumstances such that the embodiments of the invention described herein are, for example, capable of operation in other orientations than those illustrated or otherwise described herein.

Unless stated otherwise, terms such as "first" and "second" are used to arbitrarily distinguish between the elements such terms describe. Thus, these terms are not necessarily intended to indicate temporal or other prioritization of such elements. Further, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles.

Although the invention is described herein with reference to specific embodiments, various modifications and changes can be made without departing from the scope of the present invention as set forth in the claims below. Accordingly, the specification and figures are to be regarded in an illustrative rather than a restrictive sense, and all such modifications are intended to be included within the scope of the present invention. Any benefits, advantages, or solutions to problems that are described herein with regard to specific embodiments are not intended to be construed as a critical, required, or essential feature or element of any or all the claims.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

In this specification including any claims, the term "each" may be used to refer to one or more specified characteristics of a plurality of previously recited elements or steps. When used with the open-ended term "comprising," the recitation of the term "each" does not exclude additional, unrecited elements or steps. Thus, it will be understood that an apparatus may have additional, unrecited elements and a method may have additional, unrecited steps, where the additional, unrecited elements or steps do not have the one or more specified characteristics.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

The embodiments covered by the claims in this application are limited to embodiments that: (1) are enabled by this specification and (2) correspond to statutory subject matter. Non-enabled embodiments and embodiments that correspond to non-statutory subject matter are explicitly disclaimed even if they fall within the scope of the claims.

It is to be understood, however, that even though numerous characteristics and advantages of the present invention have been set forth in the foregoing description, together with details of the method, composition and function of the invention, the disclosure is illustrative only, and changes may be made in detail, within the principles of the invention to the full extent indicated by the broad general meaning of the terms in which the appended claims are expressed.

Other embodiments of the present disclosure will be apparent to those skilled in the art from consideration of the specification and practice of the embodiments disclosed herein. The foregoing embodiments are susceptible to considerable variation in practice. Accordingly, the embodiments are not intended to be limited to the specific exemplifications set forth hereinabove. It is intended that the specification and examples be considered as exemplary only, with a true scope of the disclosure being indicated by the following claims.

All documents mentioned herein are hereby incorporated by reference in their entirety or alternatively to provide the disclosure for which they were specifically relied upon.

The applicant(s) do not intend to dedicate any disclosed embodiments to the public, and to the extent any disclosed modifications or alterations may not literally fall within the scope of the claims, they are considered to be part hereof under the doctrine of equivalents.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A piezoelectric biochip for detecting one or more analytes in a liquid, said piezoelectric biochip comprising a substrate and a plurality of biosensors in fluidic channels, wherein,
    the substrate comprises:
        i) a piezoelectric material,
        ii) a substrate top surface and
        iii) a substrate bottom surface,
    each of said fluidic channels comprises:
        i) a top fluidic inlet,
        ii a top fluidic outlet,
        iii) a top fluidic channel formed in the substrate top surface and having one of the plurality of biosensors therein, and said top fluidic channel is configured to permit said liquid to traverse from the top fluidic inlet to the top fluidic outlet,
        iv) a bottom fluidic inlet,
        v) a bottom fluidic outlet, and
        vi) a bottom well formed in the substrate bottom surface and having one of the plurality of biosensors therein, or a bottom fluidic channel formed in the substrate bottom surface and having one of the plurality of biosensors therein, and said bottom fluidic channel is configured to permit said liquid to traverse from the bottom fluidic inlet to the bottom fluidic outlet, and said bottom fluidic channel, or said bottom well is located below the top fluidic channel between the bottom fluidic inlet and the bottom fluidic outlet; and
    the biosensor in the top fluidic channel comprises:
        i) a top electrode formed within the top fluidic channel on the substrate top surface and located above the bottom fluidic channel or the bottom well;
        ii) a top electrical trace formed on the substrate top surface and traversing from a top-electrode tap to the top electrode; and the biosensor in the bottom well or bottom fluidic channel comprises:
        i) a bottom electrode formed within the bottom well or bottom fluidic channel on the substrate bottom surface and located below the top electrode; and
        ii) a bottom electrical trace formed on the substrate bottom surface and traversing from a bottom-electrode tap to the bottom electrode, and
        wherein the plurality of biosensors have a resonant frequency of at least 50 MHz, and
        the top fluidic channel is fluidically isolated from the bottom fluidic channel or the bottom well.

2. The biochip of claim 1, wherein each of the one or more biosensors is an acoustical transducer having a resonant frequency greater than or equal to 200 MHz.

3. The biochip of claim 1, wherein each of the one or more biosensors has a quality factor greater than 1000 in air.

4. The biochip of claim 1, wherein one of the top and bottom electrical traces extends to and around an edge of the substrate such that both of the top-electrode and bottom-electrode taps are located on the same substrate surface.

5. The biochip of claim 1, wherein:
    the top channel inlet and outlet are uncovered; and
    the top fluidic channel is covered between the top channel inlet and outlet.

6. The biochip as claimed in claim 1, wherein the biochip comprises the bottom fluidic channel and two or more of said biosensors are located in each of said fluidic channels.

7. The biochip of claim 6, comprising two or more of said fluidic channels.

8. The biochip of claim 6, wherein two or more of said biosensors share a single top electrical trace structure.

9. The biochip of claim 8, wherein two or more of said biosensors share a single bottom electrical trace structure.

10. The biochip of claim 8, wherein the two or more biosensors have independent electrical traces.

11. An article comprising a plurality of the biochips of claim 6.

12. The article of claim 11, wherein the plurality of biochips are configured in a three-dimensional arrangement.

13. The biochip of claim 1, wherein the one or more biosensors are configured for operation in thickness shear mode.

14. The biochip of claim 13, wherein the piezoelectric material comprises AT-cut quartz crystal.

15. A method for characterizing a presence of a first analyte in a liquid using a biochip having a plurality of biosensors as claimed in claim 1, the method comprising:
    (a) applying the liquid to the top fluidic inlet of the top fluidic channel such that the liquid flows along the top fluidic channel to the top electrode of one said biosensor;
    (b) applying an alternating electrical signal across the top-electrode of said biosensor and bottom-electrode taps associated with said biosensor;
    (c) characterizing a vibration frequency of said biosensor resulting from applying the alternating electrical signal; and
    (d) characterizing the presence of the first analyte in the liquid based on the vibration frequency of said biosensor.

16. The method of claim 15, wherein:
    the liquid comprises first functionalized magnetic particles that bind to the first analyte;
    a first substance that binds to the first analyte is applied to the top electrode of said biosensor; and
    step (a) further comprises applying a first magnetic field to said biosensor to attract the first functionalized magnetic particles towards the top electrode of the biosensor, such that first functionalized magnetic particles having the bound first analyte will bind to the first substance on the top electrode.

17. The method of claim 16, wherein:
    the liquid further comprises second functionalized magnetic particles that bind to a second analyte;
    a second substance that binds to the second analyte, is applied to the top electrode of a second said biosensor;
    step (a) further comprises:
        applying the liquid comprising the second functionalized magnetic particles to the top fluidic inlet of the top fluidic channel of the second biosensor such that the liquid comprising the second functionalized magnetic particles flows along the top fluidic channel onto the top electrode of the second biosensor; and applying a second magnetic field to the second biosensor to attract the second functionalized magnetic particles towards the top electrode of the second biosensor, such that second functionalized magnetic particles having the bound second analyte will bind to the second substance on the top electrode of the second biosensor;

step (b) further comprises applying an alternating electrical signal across the top-electrode and bottom-electrode taps associated with the second biosensor;

step (c) further comprises characterizing a vibration frequency of the second biosensor resulting from applying the alternating electrical signal across the top-electrode and bottom-electrode taps associated with the second biosensor; and step (d) further comprises characterizing the presence of the second analyte in the liquid based on the vibration frequency of the second biosensor.

* * * * *